(12) United States Patent
Kouzuma et al.

(10) Patent No.: US 7,250,269 B2
(45) Date of Patent: Jul. 31, 2007

(54) COMPOSITION FOR ASSAYING GLYCOPROTEIN

(75) Inventors: Takuji Kouzuma, Mishima (JP); Issei Yoshioka, Shizuoka (JP); Motoo Arai, Sakai (JP); Junichi Sumitani, Sakai (JP); Shigeyuki Imamura, Shizuoka (JP)

(73) Assignee: Asahi Kasei Pharma Corporation, Osaka (JP)

(*) Notice: Subject to any disclaimer, the term of this patent is extended or adjusted under 35 U.S.C. 154(b) by 172 days.

(21) Appl. No.: 10/470,678

(22) PCT Filed: Jan. 30, 2002

(86) PCT No.: PCT/JP02/00721

§ 371 (c)(1),
(2), (4) Date: Sep. 15, 2003

(87) PCT Pub. No.: WO02/061119

PCT Pub. Date: Aug. 8, 2002

(65) Prior Publication Data

US 2005/0101771 A1    May 12, 2005

(30) Foreign Application Priority Data

| Jan. 31, 2001 | (JP) | ............................. 2001-022953 |
| Feb. 16, 2001 | (JP) | ............................. 2001-039796 |
| Aug. 8, 2001  | (JP) | ............................. 2001-240002 |

(51) Int. Cl.
*C12Q 1/26* (2006.01)
*C12N 9/06* (2006.01)

(52) U.S. Cl. ........................................ 435/25; 435/191

(58) Field of Classification Search .................... None
See application file for complete search history.

(56) References Cited

U.S. PATENT DOCUMENTS

| 5,156,947 A | 10/1992 | Siedel et al. |
| 5,370,990 A | 12/1994 | Staniford et al. |
| 5,387,109 A | 2/1995  | Ishikawa et al. |
| 5,948,659 A | 9/1999  | Kato et al. |
| 5,972,671 A | 10/1999 | Kato et al. |
| 6,008,006 A | 12/1999 | Torrens et al. |
| 6,127,138 A | 10/2000 | Ishimaru et al. |
| 6,444,724 B1 | 9/2002 | Stangel et al. |

FOREIGN PATENT DOCUMENTS

| EP | 0 526 150 A1 | 2/1993 |
| EP | 0 921 198 A1 | 6/1999 |
| JP | 61-94663 A | 5/1986 |
| JP | 2-195899 A | 8/1990 |
| JP | 2-195900 A | 8/1990 |
| JP | 10-201473 A | 8/1998 |
| JP | 10-232233 A | 9/1998 |
| JP | 10-262695 | * 10/1998 |
| JP | 11-155596 A | 6/1999 |
| JP | 11-243950 A | 9/1999 |
| JP | WO00-50579 | * 8/2000 |
| JP | 2000-342252 A | 12/2000 |
| JP | 2001-54398 A | 2/2001 |
| JP | 2001-054398 A | 2/2001 |
| JP | 2001-215229 A | 8/2001 |
| JP | 2001-258593 A | 9/2001 |
| WO | WO 97/13872 A1 | 4/1997 |

OTHER PUBLICATIONS

S. Rodriguez-Segade et al., Clinical Chemistry, vol. 35, No. 1, pp. 134-138 (1989).
Rinsho Kagaku, 27, pp. 99-106 (1988) (with English summary and partial English translation).
Yoshida et al., European Journal of Biochemistry, vol. 242, No. 3, 1996, pp. 499-505.
Sakai et al., FEBS Letters, 459 (1999) 233-237.

* cited by examiner

*Primary Examiner*—Robert A. Wax
(74) *Attorney, Agent, or Firm*—Birch, Stewart, Kolasch & Birch, LLP

(57) ABSTRACT

Compositions for accurately assaying a glycated protein by: 1) avoiding effects of globulin and ascorbic acid components, 2) siabilizing proteases and at least enzymes acting on glycated amino acids; 3) accurately assaying albumin; and 4) assaying glycated albumin while avoiding the effects of glycated hemoglobin, and an assay method are provided. Thus, the contents of a glycated protein and glycated albumin can be more accurately determined.

20 Claims, 5 Drawing Sheets

Fig. 3  Linearity in GA assay
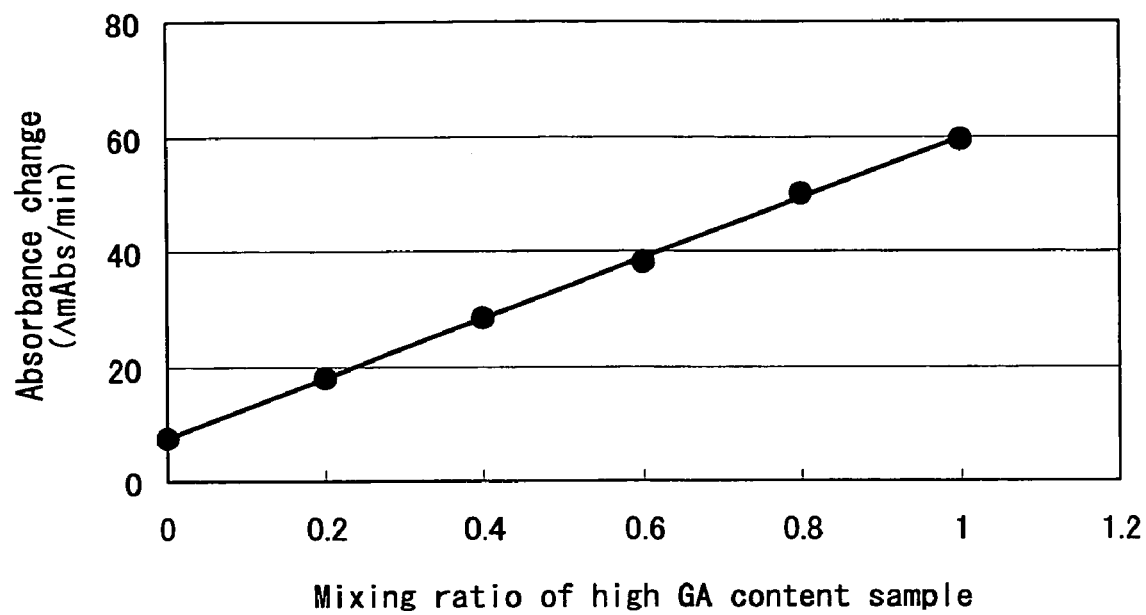
Fig. 4  Effect of buffer agent on stability of ascorbic acid elimination performance
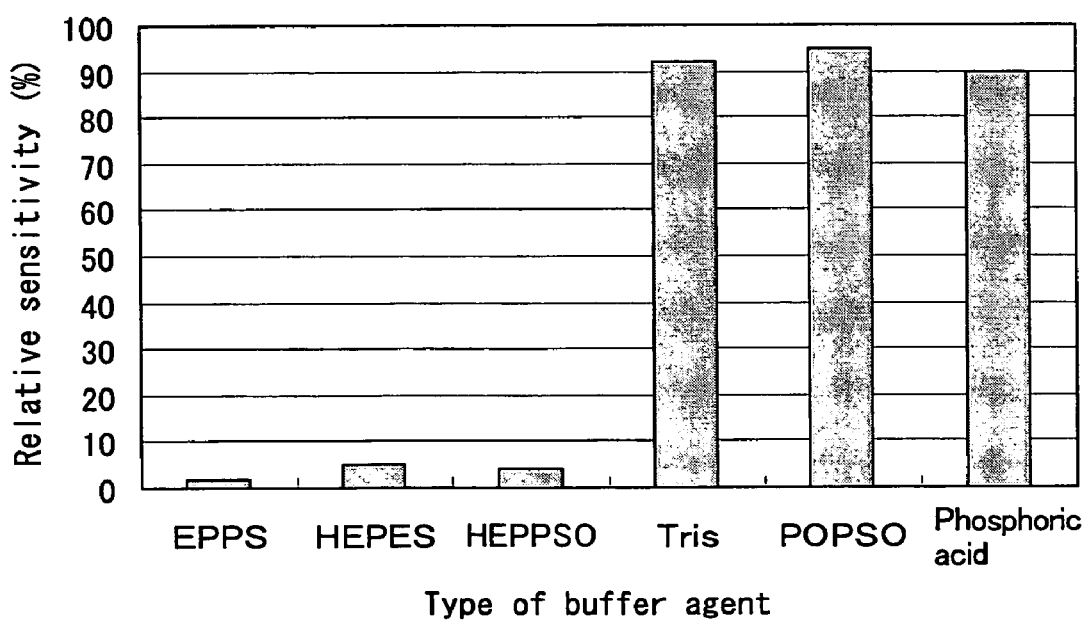

Fig. 5 Effect of stabilizer and storage stability of pretreatment reagent
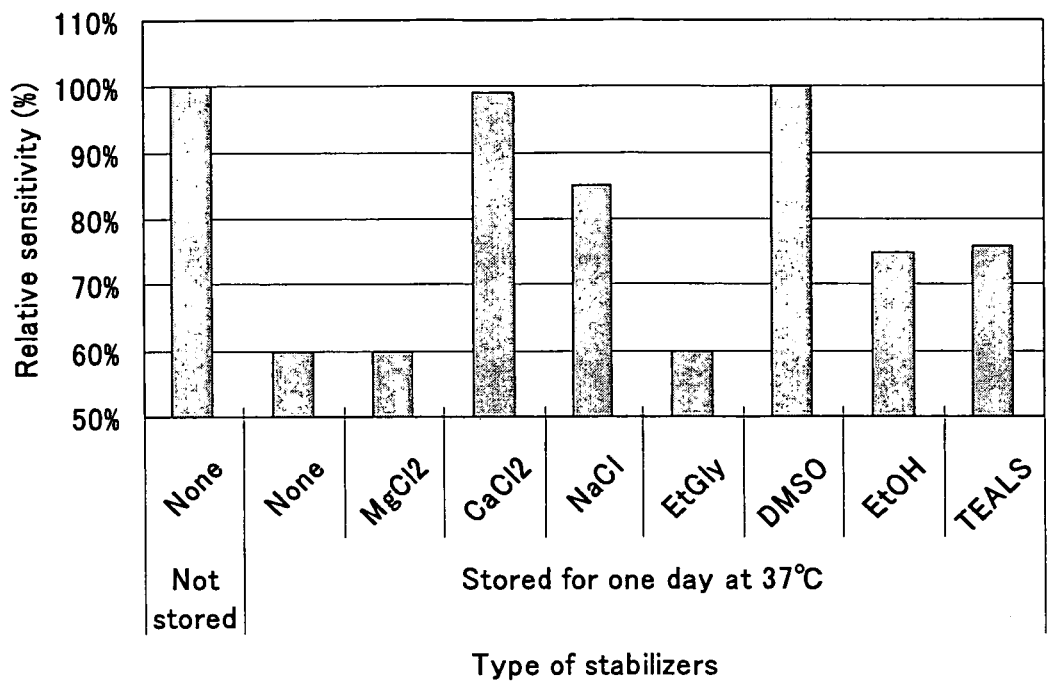
Fig. 6 Stabilization of glycated amino acid stabilizer
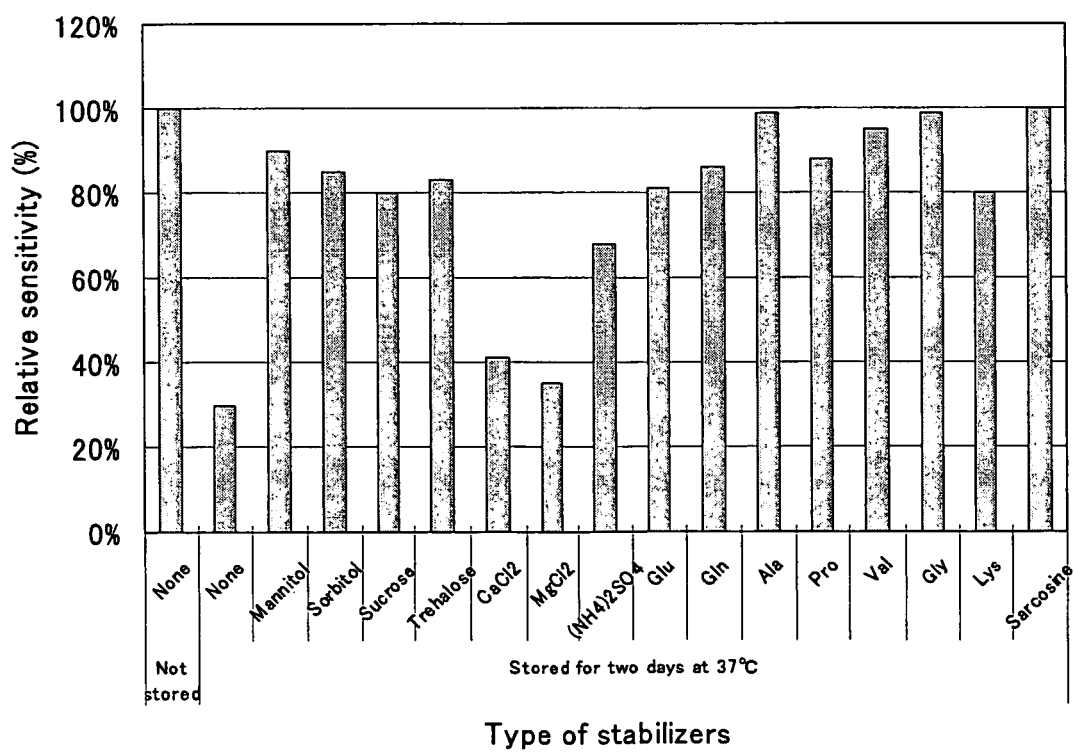

Fig. 9   Correlation between HPLC method and enzymatic method
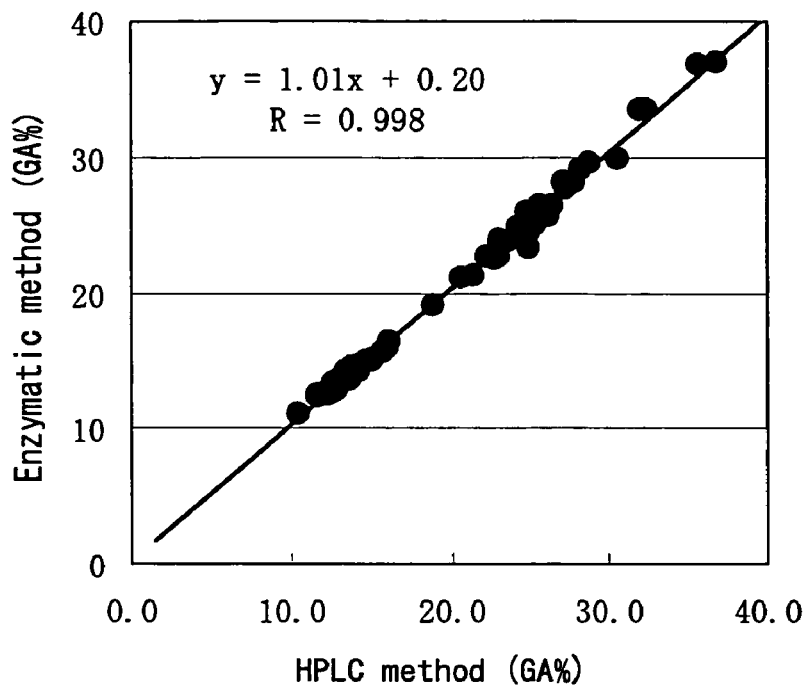
Fig. 10   Reaction curve for composition using second reagent containing protease
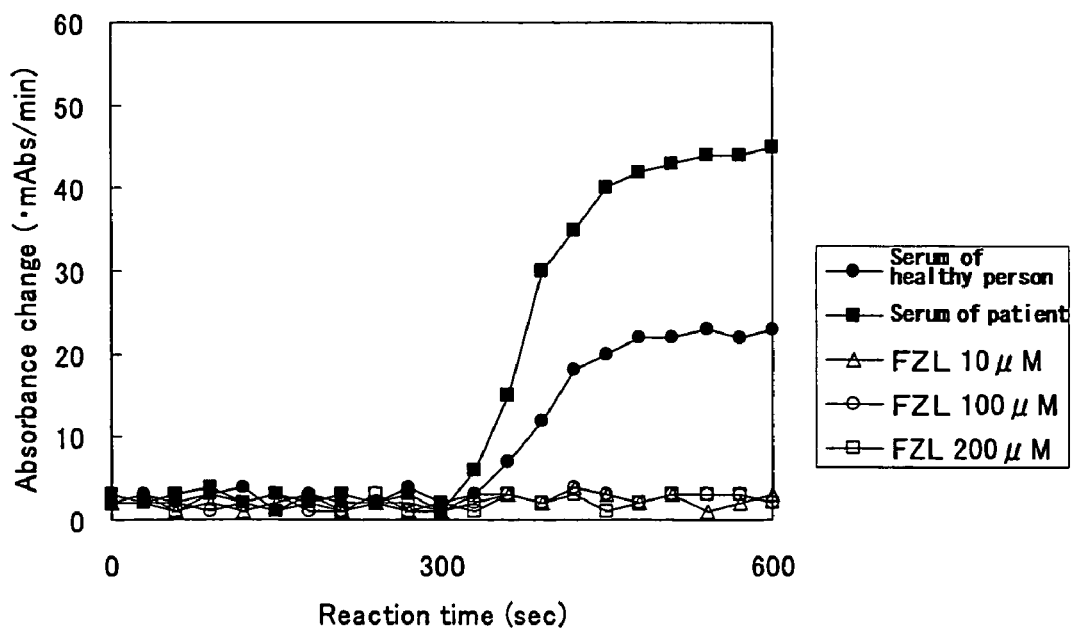

SEQUENCE LISTING

```
<160> NUMBER OF SEQ ID NOS: 10

<210> SEQ ID NO 1
<211> LENGTH: 1320
<212> TYPE: DNA
<213> ORGANISM: Fusarium oxysporum IFO-9722
<220> FEATURE:
<221> NAME/KEY: CDS
<222> LOCATION: (1)..(1320)
<300> PUBLICATION INFORMATION:
<308> DATABASE ACCESSION NUMBER: DDBJ E16562
<309> DATABASE ENTRY DATE: 1999-07-28
<310> PATENT DOCUMENT NUMBER: JP 1998201473-A/1
<311> PATENT FILING DATE: 1997-01-20
<312> PUBLICATION DATE: 1998-08-04

<400> SEQUENCE: 1 gcc tca act ctc acc aaa cag tcc caa att ctc atc gtt ggt ggc gga        48
Ala Ser Thr Leu Thr Lys Gln Ser Gln Ile Leu Ile Val Gly Gly Gly
1               5                   10                  15 act tgg gga tgc tca act gcc ctc cat ctc gcc cgt cgg ggt tac acc        96
Thr Trp Gly Cys Ser Thr Ala Leu His Leu Ala Arg Arg Gly Tyr Thr
            20                  25                  30 aac gtc act gtt ctc gat gtc aat cgc atc ccg tca ccg ata tca gcc       144
Asn Val Thr Val Leu Asp Val Asn Arg Ile Pro Ser Pro Ile Ser Ala
        35                  40                  45 ggg cat gat gta aac aaa ctt gct ggc cga ctg tcg act gcc gat agc       192
Gly His Asp Val Asn Lys Leu Ala Gly Arg Leu Ser Thr Ala Asp Ser
    50                  55                  60 aaa ggt gat gat gaa gac tca atc tgg aaa gca ctt agc tac gcc gca       240
Lys Gly Asp Asp Glu Asp Ser Ile Trp Lys Ala Leu Ser Tyr Ala Ala
65                  70                  75                  80 gct caa gga tgg ctc cac gac cct gtc ttc caa cca ttc tgc cac aat       288
Ala Gln Gly Trp Leu His Asp Pro Val Phe Gln Pro Phe Cys His Asn
                85                  90                  95
```

-continued

| | |
|---|---|
| aca ggc tct gtc gtg gct ggc tca aca cca aag tct atc aag cag ctg<br>Thr Gly Ser Val Val Ala Gly Ser Thr Pro Lys Ser Ile Lys Gln Leu<br>          100                   105                   110 | 336 |
| gta gaa gat gag atc ggt gac gac atc gac cag tat aca cct ctc aac<br>Val Glu Asp Glu Ile Gly Asp Asp Ile Asp Gln Tyr Thr Pro Leu Asn<br>115                   120                   125 | 384 |
| aca gca gaa gat ttc aga aag acc atg cct gag ggt atc ctg aca ggt<br>Thr Ala Glu Asp Phe Arg Lys Thr Met Pro Glu Gly Ile Leu Thr Gly<br>130                   135                   140 | 432 |
| aac ttt cca ggc tgg aag ggc ttt tac aag ccc acg ggt tct ggt tgg<br>Asn Phe Pro Gly Trp Lys Gly Phe Tyr Lys Pro Thr Gly Ser Gly Trp<br>145                   150                   155                   160 | 480 |
| gtt cat gct cga aaa gct atg aaa gct gct ttc gaa gag agc gag agg<br>Val His Ala Arg Lys Ala Met Lys Ala Ala Phe Glu Glu Ser Glu Arg<br>          165                   170                   175 | 528 |
| ctt ggt gtc aaa ttc atc act ggc tct ccc gaa gga aag gtg gag agt<br>Leu Gly Val Lys Phe Ile Thr Gly Ser Pro Glu Gly Lys Val Glu Ser<br>          180                   185                   190 | 576 |
| ctg atc ttt gaa gac ggc gat gtt cga ggt gcc aag acg gca gat ggt<br>Leu Ile Phe Glu Asp Gly Asp Val Arg Gly Ala Lys Thr Ala Asp Gly<br>          195                   200                   205 | 624 |
| aag gag cac aga gcg gat cga act att ctt tcc gct ggt gct tca gca<br>Lys Glu His Arg Ala Asp Arg Thr Ile Leu Ser Ala Gly Ala Ser Ala<br>210                   215                   220 | 672 |
| gag ttc ttc ctc gat ttt gag aac cag atc cag cct acg gcg tgg acc<br>Glu Phe Phe Leu Asp Phe Glu Asn Gln Ile Gln Pro Thr Ala Trp Thr<br>225                   230                   235                   240 | 720 |
| ctg ggc cat atc cag atg aca cca gaa gaa acc aag ctg tac aag aac<br>Leu Gly His Ile Gln Met Thr Pro Glu Glu Thr Lys Leu Tyr Lys Asn<br>                   245                   250                   255 | 768 |
| ctg cca cct ctt ttc aac atc aac caa ggt ttc ttc atg gaa cct gat<br>Leu Pro Pro Leu Phe Asn Ile Asn Gln Gly Phe Phe Met Glu Pro Asp<br>          260                   265                   270 | 816 |
| gag gat ctt cat caa ctc aag atg tgc gat gaa cat ccg ggc tac tgc<br>Glu Asp Leu His Gln Leu Lys Met Cys Asp Glu His Pro Gly Tyr Cys<br>          275                   280                   285 | 864 |
| aac tgg gtt gaa aag cct ggt tct aag tac ccc cag tcc atc ccc ttc<br>Asn Trp Val Glu Lys Pro Gly Ser Lys Tyr Pro Gln Ser Ile Pro Phe<br>          290                   295                   300 | 912 |
| gca aag cat caa gtg cca acc gag gct gaa cga cgc atg aag cag ttt<br>Ala Lys His Gln Val Pro Thr Glu Ala Glu Arg Arg Met Lys Gln Phe<br>305                   310                   315                   320 | 960 |
| ctg aaa gat atc atg cct cag ctt gca gat cgg ccg ctt gtt cat gct<br>Leu Lys Asp Ile Met Pro Gln Leu Ala Asp Arg Pro Leu Val His Ala<br>                   325                   330                   335 | 1008 |
| cga atc tgc tgg tgc gct gat aca cag gat aga atg ttc ctg atc acc<br>Arg Ile Cys Trp Cys Ala Asp Thr Gln Asp Arg Met Phe Leu Ile Thr<br>          340                   345                   350 | 1056 |
| tat cat cct cga cat ccc tca ctt gtc att gct tca ggt gat tgc ggc<br>Tyr His Pro Arg His Pro Ser Leu Val Ile Ala Ser Gly Asp Cys Gly<br>                   355                   360                   365 | 1104 |
| acg ggt tac aag cat atc aca tca att gga aag ttc atc tct gac tgt<br>Thr Gly Tyr Lys His Ile Thr Ser Ile Gly Lys Phe Ile Ser Asp Cys<br>          370                   375                   380 | 1152 |
| atg gag ggt acg ctt gag gaa agg ttt gcc aag ttc tgg aga tgg cga<br>Met Glu Gly Thr Leu Glu Glu Arg Phe Ala Lys Phe Trp Arg Trp Arg<br>385                   390                   395                   400 | 1200 |
| cca gag aag ttt acc gag ttc tgg ggt aaa gat cct ctg gat cgg ttt<br>Pro Glu Lys Phe Thr Glu Phe Trp Gly Lys Asp Pro Leu Asp Arg Phe<br>                   405                   410                   415 | 1248 |

```
gga gct gac gat aag atc atg gat ttg ccc aag agt gat gta gag gga      1296
Gly Ala Asp Asp Lys Ile Met Asp Leu Pro Lys Ser Asp Val Glu Gly
        420                 425                 430 tgg aca aat atc aag aat gat atc                                      1320
Trp Thr Asn Ile Lys Asn Asp Ile
        435                 440

<210> SEQ ID NO 2
<211> LENGTH: 1320
<212> TYPE: DNA
<213> ORGANISM: Artificial Sequence
<220> FEATURE:
<223> OTHER INFORMATION: sequence derived from Fusarium oxysporum IFO-
      9722
<220> FEATURE:
<221

```
                                              -continued

Lys Glu His Arg Ala Asp Arg Thr Ile Leu Ser Ala Gly Ala Ser Ala
    210                 215                 220 gag ttc ttc ctc gat ttt gag aac cag atc cag cct acg gcg tgg acc      720
Glu Phe Phe Leu Asp Phe Glu Asn Gln Ile Gln Pro Thr Ala Trp Thr
225                 230                 235                 240 ctg ggc cat atc cag atg aca cca gaa gaa acc aag ctg tac aag aac      768
Leu Gly His Ile Gln Met Thr Pro Glu Glu Thr Lys Leu Tyr Lys Asn
                245                 250                 255 ctg cca cct ctt ttc aac atc aac caa ggt ttc ttc atg gaa cct gat      816
Leu Pro Pro Leu Phe Asn Ile Asn Gln Gly Phe Phe Met Glu Pro Asp
            260                 265                 270 gag gat ctt cat caa ctc aag atg tgc gat gaa cat ccg ggc tac tgc      864
Glu Asp Leu His Gln Leu Lys Met Cys Asp Glu His Pro Gly Tyr Cys
        275                 280                 285 aac tgg gtt gaa aag cct ggt tct aag tac ccc cag tcc atc ccc ttc      912
Asn Trp Val Glu Lys Pro Gly Ser Lys Tyr Pro Gln Ser Ile Pro Phe
    290                 295                 300 gca aag cat caa gtg cca acc gag gct gaa cga cgc atg aag cag ttt      960
Ala Lys His Gln Val Pro Thr Glu Ala Glu Arg Arg Met Lys Gln Phe
305                 310                 315                 320 ctg aaa gat atc atg cct cag ctt gca gat cgg ccg ctt gtt cat gct     1008
Leu Lys Asp Ile Met Pro Gln Leu Ala Asp Arg Pro Leu Val His Ala
                325                 330                 335 cga atc tgc tgg tgc gct gat aca cag gat aga atg ttc ctg atc acc     1056
Arg Ile Cys Trp Cys Ala Asp Thr Gln Asp Arg Met Phe Leu Ile Thr
            340                 345                 350 tat cat cct cga cat ccc tca ctt gtc att gct tca ggt gat tgc ggc     1104
Tyr His Pro Arg His Pro Ser Leu Val Ile Ala Ser Gly Asp Cys Gly
        355                 360                 365 acg ggt tac tgg cat atc aca tca att gga aag ttc atc tct gac tgt     1152
Thr Gly Tyr Trp His Ile Thr Ser Ile Gly Lys Phe Ile Ser Asp Cys
    370                 375                 380 atg gag ggt acg ctt gag gaa agg ttt gcc aag ttc tgg aga tgg cga     1200
Met Glu Gly Thr Leu Glu Glu Arg Phe Ala Lys Phe Trp Arg Trp Arg
385                 390                 395                 400 cca gag aag ttt acc gag ttc tgg ggt aaa gat cct ctg gat cgg ttt     1248
Pro Glu Lys Phe Thr Glu Phe Trp Gly Lys Asp Pro Leu Asp Arg Phe
                405                 410                 415 gga gct gac gat aag atc atg gat ttg ccc aag agt gat gta gag gga     1296
Gly Ala Asp Asp Lys Ile Met Asp Leu Pro Lys Ser Asp Val Glu Gly
            420                 425                 430 tgg aca aat atc aag aat gat atc                                     1320
Trp Thr Asn Ile Lys Asn Asp Ile
        435                 440

<210> SEQ ID NO 3
<211> LENGTH: 1320
<212> TYPE: DNA
<213> ORGANISM: Artificial Sequence
<220> FEATURE:
<223> OTHER INFORMATION: sequence derived from Fusarium oxysporum IFO-
      9722
<220> FEATURE:
<221> NAME/KEY: CDS
<222> LOCATION: (1)..(1320)
<220> FEATURE:
<221> NAME/KEY: mutation
<222> LOCATION: (1115)..(1115)

<400> SEQUENCE: 3 gcc tca act ctc acc aaa cag tcc caa att ctc atc gtt ggt ggc gga       48
Ala Ser Thr Leu Thr Lys Gln Ser Gln Ile Leu Ile Val Gly Gly Gly
1               5                   10                  15
```

-continued

| | | |
|---|---|---|
| act tgg gga tgc tca act gcc ctc cat ctc gcc cgt cgg ggt tac acc<br>Thr Trp Gly Cys Ser Thr Ala Leu His Leu Ala Arg Arg Gly Tyr Thr<br>            20                  25                  30 | | 96 |
| aac gtc act gtt ctc gat gtc aat cgc atc ccg tca ccg ata tca gcc<br>Asn Val Thr Val Leu Asp Val Asn Arg Ile Pro Ser Pro Ile Ser Ala<br>        35                  40                  45 | | 144 |
| ggg cat gat gta aac aaa ctt gct ggc cga ctg tcg act gcc gat agc<br>Gly His Asp Val Asn Lys Leu Ala Gly Arg Leu Ser Thr Ala Asp Ser<br>    50                  55                  60 | | 192 |
| aaa ggt gat gat gaa gac tca atc tgg aaa gca ctt agc tac gcc gca<br>Lys Gly Asp Asp Glu Asp Ser Ile Trp Lys Ala Leu Ser Tyr Ala Ala<br>65                  70                  75                  80 | | 240 |
| gct caa gga tgg ctc cac gac cct gtc ttc caa cca ttc tgc cac aat<br>Ala Gln Gly Trp Leu His Asp Pro Val Phe Gln Pro Phe Cys His Asn<br>                85                  90                  95 | | 288 |
| aca ggc tct gtc gtg gct ggc tca aca cca aag tct atc aag cag ctg<br>Thr Gly Ser Val Val Ala Gly Ser Thr Pro Lys Ser Ile Lys Gln Leu<br>            100                 105                 110 | | 336 |
| gta gaa gat gag atc ggt gac gac atc gac cag tat aca cct ctc aac<br>Val Glu Asp Glu Ile Gly Asp Asp Ile Asp Gln Tyr Thr Pro Leu Asn<br>        115                 120                 125 | | 384 |
| aca gca gaa gat ttc aga aag acc atg cct gag ggt atc ctg aca ggt<br>Thr Ala Glu Asp Phe Arg Lys Thr Met Pro Glu Gly Ile Leu Thr Gly<br>    130                 135                 140 | | 432 |
| aac ttt cca ggc tgg aag ggc ttt tac aag ccc acg ggt tct ggt tgg<br>Asn Phe Pro Gly Trp Lys Gly Phe Tyr Lys Pro Thr Gly Ser Gly Trp<br>145                 150                 155                 160 | | 480 |
| gtt cat gct cga aaa gct atg aaa gct gct ttc gaa gag agc gag agg<br>Val His Ala Arg Lys Ala Met Lys Ala Ala Phe Glu Glu Ser Glu Arg<br>                165                 170                 175 | | 528 |
| ctt ggt gtc aaa ttc atc act ggc tct ccc gaa gga aag gtg gag agt<br>Leu Gly Val Lys Phe Ile Thr Gly Ser Pro Glu Gly Lys Val Glu Ser<br>            180                 185                 190 | | 576 |
| ctg atc ttt gaa gac ggc gat gtt cga ggt gcc aag acg gca gat ggt<br>Leu Ile Phe Glu Asp Gly Asp Val Arg Gly Ala Lys Thr Ala Asp Gly<br>        195                 200                 205 | | 624 |
| aag gag cac aga gcg gat cga act att ctt tcc gct ggt gct tca gca<br>Lys Glu His Arg Ala Asp Arg Thr Ile Leu Ser Ala Gly Ala Ser Ala<br>    210                 215                 220 | | 672 |
| gag ttc ttc ctc gat ttt gag aac cag atc cag cct acg gcg tgg acc<br>Glu Phe Phe Leu Asp Phe Glu Asn Gln Ile Gln Pro Thr Ala Trp Thr<br>225                 230                 235                 240 | | 720 |
| ctg ggc cat atc cag atg aca cca gaa gaa acc aag ctg tac aag aac<br>Leu Gly His Ile Gln Met Thr Pro Glu Glu Thr Lys Leu Tyr Lys Asn<br>                245                 250                 255 | | 768 |
| ctg cca cct ctt ttc aac atc aac caa ggt ttc ttc atg gaa cct gat<br>Leu Pro Pro Leu Phe Asn Ile Asn Gln Gly Phe Phe Met Glu Pro Asp<br>            260                 265                 270 | | 816 |
| gag gat ctt cat caa ctc aag atg tgc gat gaa cat ccg ggc tac tgc<br>Glu Asp Leu His Gln Leu Lys Met Cys Asp Glu His Pro Gly Tyr Cys<br>        275                 280                 285 | | 864 |
| aac tgg gtt gaa aag cct ggt tct aag tac ccc cag tcc atc ccc ttc<br>Asn Trp Val Glu Lys Pro Gly Ser Lys Tyr Pro Gln Ser Ile Pro Phe<br>    290                 295                 300 | | 912 |
| gca aag cat caa gtg cca acc gag gct gaa cga cgc atg aag cag ttt<br>Ala Lys His Gln Val Pro Thr Glu Ala Glu Arg Arg Met Lys Gln Phe<br>305                 310                 315                 320 | | 960 |
| ctg aaa gat atc atg cct cag ctt gca gat cgg ccg ctt gtt cat gct<br>Leu Lys Asp Ile Met Pro Gln Leu Ala Asp Arg Pro Leu Val His Ala | | 1008 |

-continued

```
                       325                 330                 335
cga atc tgc tgg tgc gct gat aca cag gat aga atg ttc ctg atc acc    1056
Arg Ile Cys Trp Cys Ala Asp Thr Gln Asp Arg Met Phe Leu Ile Thr
        340                 345                 350 tat cat cct cga cat ccc tca ctt gtc att gct tca ggt gat tgc ggc    1104
Tyr His Pro Arg His Pro Ser Leu Val Ile Ala Ser Gly Asp Cys Gly
            355                 360                 365 acg ggt tac atg cat atc aca tca att gga aag ttc atc tct gac tgt    1152
Thr Gly Tyr Met His Ile Thr Ser Ile Gly Lys Phe Ile Ser Asp Cys
370                 375                 380 atg gag ggt acg ctt gag gaa agg ttt gcc aag ttc tgg aga tgg cga    1200
Met Glu Gly Thr Leu Glu Glu Arg Phe Ala Lys Phe Trp Arg Trp Arg
385                 390                 395                 400 cca gag aag ttt acc gag ttc tgg ggt aaa gat cct ctg gat cgg ttt    1248
Pro Glu Lys Phe Thr Glu Phe Trp Gly Lys Asp Pro Leu Asp Arg Phe
                405                 410                 415 gga gct gac gat aag atc atg gat ttg ccc aag agt gat gta gag gga    1296
Gly Ala Asp Asp Lys Ile Met Asp Leu Pro Lys Ser Asp Val Glu Gly
            420                 425                 430 tgg aca aat atc aag aat gat atc                                    1320
Trp Thr Asn Ile Lys Asn Asp Ile
        435                 440

<210> SEQ ID NO 4
<211> LENGTH: 1320
<212> TYPE: DNA
<213> ORGANISM: Artificial Sequence
<220> FEATURE:
<223> OTHER INFORMATION: sequence derived from Fusarium oxysporum IFO-
      9722
<220> FEATURE:
<221> NAME/KEY: CDS
<222> LOCATION: (1)..(1320)
<220> FEATURE:
<221> NAME/KEY: mutation
<222> LOCATION: (1114)..(1115)

<400> SEQUENCE: 4 gcc tca act ctc acc aaa cag tcc caa att ctc atc gtt ggt ggc gga      48
Ala Ser Thr Leu Thr Lys Gln Ser Gln Ile Leu Ile Val Gly Gly Gly
1               5                   10                  15 act tgg gga tgc tca act gcc ctc cat ctc gcc cgt cgg ggt tac acc      96
Thr Trp Gly Cys Ser Thr Ala Leu His Leu Ala Arg Arg Gly Tyr Thr
            20                  25                  30 aac gtc act gtt ctc gat gtc aat cgc atc ccg tca ccg ata tca gcc     144
Asn Val Thr Val Leu Asp Val Asn Arg Ile Pro Ser Pro Ile Ser Ala
        35                  40                  45 ggg cat gat gta aac aaa ctt gct ggc cga ctg tcg act gcc gat agc     192
Gly His Asp Val Asn Lys Leu Ala Gly Arg Leu Ser Thr Ala Asp Ser
    50                  55                  60 aaa ggt gat gat gaa gac tca atc tgg aaa gca ctt agc tac gcc gca     240
Lys Gly Asp Asp Glu Asp Ser Ile Trp Lys Ala Leu Ser Tyr Ala Ala
65                  70                  75                  80 gct caa gga tgg ctc cac gac cct gtc ttc caa cca ttc tgc cac aat     288
Ala Gln Gly Trp Leu His Asp Pro Val Phe Gln Pro Phe Cys His Asn
                85                  90                  95 aca ggc tct gtc gtg gct ggc tca aca cca aag tct atc aag cag ctg     336
Thr Gly Ser Val Val Ala Gly Ser Thr Pro Lys Ser Ile Lys Gln Leu
            100                 105                 110 gta gaa gat gag atc ggt gac gac atc gac cag tat aca cct ctc aac     384
Val Glu Asp Glu Ile Gly Asp Asp Ile Asp Gln Tyr Thr Pro Leu Asn
        115                 120                 125
```

```
aca gca gaa gat ttc aga aag acc atg cct gag ggt atc ctg aca ggt      432
Thr Ala Glu Asp Phe Arg Lys Thr Met Pro Glu Gly Ile Leu Thr Gly
    130                 135                 140 aac ttt cca ggc tgg aag ggc ttt tac aag ccc acg ggt tct ggt tgg      480
Asn Phe Pro Gly Trp Lys Gly Phe Tyr Lys Pro Thr Gly Ser Gly Trp
145                 150                 155                 160 gtt cat gct cga aaa gct atg aaa gct gct ttc gaa gag agc gag agg      528
Val His Ala Arg Lys Ala Met Lys Ala Ala Phe Glu Glu Ser Glu Arg
                165                 170                 175 ctt ggt gtc aaa ttc atc act ggc tct ccc gaa gga aag gtg gag agt      576
Leu Gly Val Lys Phe Ile Thr Gly Ser Pro Glu Gly Lys Val Glu Ser
            180                 185                 190 ctg atc ttt gaa gac ggc gat gtt cga ggt gcc aag acg gca gat ggt      624
Leu Ile Phe Glu Asp Gly Asp Val Arg Gly Ala Lys Thr Ala Asp Gly
        195                 200                 205 aag gag cac aga gcg gat cga act att ctt tcc gct ggt gct tca gca      672
Lys Glu His Arg Ala Asp Arg Thr Ile Leu Ser Ala Gly Ala Ser Ala
    210                 215                 220 gag ttc ttc ctc gat ttt gag aac cag atc cag cct acg gcg tgg acc      720
Glu Phe Phe Leu Asp Phe Glu Asn Gln Ile Gln Pro Thr Ala Trp Thr
225                 230                 235                 240 ctg ggc cat atc cag atg aca cca gaa gaa acc aag ctg tac aag aac      768
Leu Gly His Ile Gln Met Thr Pro Glu Glu Thr Lys Leu Tyr Lys Asn
                245                 250                 255 ctg cca cct ctt ttc aac atc aac caa ggt ttc ttc atg gaa cct gat      816
Leu Pro Pro Leu Phe Asn Ile Asn Gln Gly Phe Phe Met Glu Pro Asp
            260                 265                 270 gag gat ctt cat caa ctc aag atg tgc gat gaa cat ccg ggc tac tgc      864
Glu Asp Leu His Gln Leu Lys Met Cys Asp Glu His Pro Gly Tyr Cys
        275                 280                 285 aac tgg gtt gaa aag cct ggt tct aag tac ccc cag tcc atc ccc ttc      912
Asn Trp Val Glu Lys Pro Gly Ser Lys Tyr Pro Gln Ser Ile Pro Phe
    290                 295                 300 gca aag cat caa gtg cca acc gag gct gaa cga cgc atg aag cag ttt      960
Ala Lys His Gln Val Pro Thr Glu Ala Glu Arg Arg Met Lys Gln Phe
305                 310                 315                 320 ctg aaa gat atc atg cct cag ctt gca gat cgg ccg ctt gtt cat gct     1008
Leu Lys Asp Ile Met Pro Gln Leu Ala Asp Arg Pro Leu Val His Ala
                325                 330                 335 cga atc tgc tgg tgc gct gat aca cag gat aga atg ttc ctg atc acc     1056
Arg Ile Cys Trp Cys Ala Asp Thr Gln Asp Arg Met Phe Leu Ile Thr
            340                 345                 350 tat cat cct cga cat ccc tca ctt gtc att gct tca ggt gat tgc ggc     1104
Tyr His Pro Arg His Pro Ser Leu Val Ile Ala Ser Gly Asp Cys Gly
        355                 360                 365 acg ggt tac gtg cat atc aca tca att gga aag ttc atc tct gac tgt     1152
Thr Gly Tyr Val His Ile Thr Ser Ile Gly Lys Phe Ile Ser Asp Cys
    370                 375                 380 atg gag ggt acg ctt gag gaa agg ttt gcc aag ttc tgg aga tgg cga     1200
Met Glu Gly Thr Leu Glu Glu Arg Phe Ala Lys Phe Trp Arg Trp Arg
385                 390                 395                 400 cca gag aag ttt acc gag ttc tgg ggt aaa gat cct ctg gat cgg ttt     1248
Pro Glu Lys Phe Thr Glu Phe Trp Gly Lys Asp Pro Leu Asp Arg Phe
                405                 410                 415 gga gct gac gat aag atc atg gat ttg ccc aag agt gat gta gag gga     1296
Gly Ala Asp Asp Lys Ile Met Asp Leu Pro Lys Ser Asp Val Glu Gly
            420                 425                 430 tgg aca aat atc aag aat gat atc                                     1320
Trp Thr Asn Ile Lys Asn Asp Ile
        435                 440
```

-continued

<210> SEQ ID NO 5
<211> LENGTH: 30
<212> TYPE: DNA
<213> ORGANISM: Artificial Sequence
<220> FEATURE:
<223> OTHER INFORMATION: synthesized PCR primer

<400> SEQUENCE: 5
aaaaccatgg cctcaactct caccaaacag					30

<210> SEQ ID NO 6
<211> LENGTH: 30
<212> TYPE: DNA
<213> ORGANISM: Artificial Sequence
<220> FEATURE:
<223> OTHER INFORMATION: synthesized PCR primer

<400> SEQUENCE: 6
aaaaagaatt cagatatcat tcttgatatt					30

<210> SEQ ID NO 7
<211> LENGTH: 27
<212> TYPE: DNA
<213> ORGANISM: Artificial Sequence
<220> FEATURE:
<223> OTHER INFORMATION: Site directed mutagenesis primer
<220> FEATURE:
<221> NAME/KEY: misc_feature
<222> LOCATION: (13)..(14)
<223> OTHER INFORMATION: n is a, c, g, or t

<400> SEQUENCE: 7 ggcacggggtt acnnscatat cacatca					27

<210> SEQ ID NO 8
<211> LENGTH: 440
<212> TYPE: PRT
<213> ORGANISM: Artificial Sequence
<220> FEATURE:
<223> OTHER INFORMATION: Synthetic protein sequence of SEQ ID NO: 2
<220> FEATURE:
<221> NAME/KEY: MUTAGEN
<222> LOCATION: (372)..(372)

<400> SEQUENCE: 8

Ala Ser Thr Leu Thr Lys Gln Ser Gln Ile Leu Ile Val Gly Gly Gly
1               5                   10                  15

Thr Trp Gly Cys Ser Thr Ala Leu His Leu Ala Arg Arg Gly Tyr Thr
            20                  25                  30

Asn Val Thr Val Leu Asp Val Asn Arg Ile Pro Ser Pro Ile Ser Ala
        35                  40                  45

Gly His Asp Val Asn Lys Leu Ala Gly Arg Leu Ser Thr Ala Asp Ser
    50                  55                  60

Lys Gly Asp Asp Glu Asp Ser Ile Trp Lys Ala Leu Ser Tyr Ala Ala
65                  70                  75                  80

Ala Gln Gly Trp Leu His Asp Pro Val Phe Gln Pro Phe Cys His Asn
                85                  90                  95

Thr Gly Ser Val Val Ala Gly Ser Thr Pro Lys Ser Ile Lys Gln Leu
            100                 105                 110

Val Glu Asp Glu Ile Gly Asp Ile Asp Gln Tyr Thr Pro Leu Asn
        115                 120                 125

Thr Ala Glu Asp Phe Arg Lys Thr Met Pro Glu Gly Ile Leu Thr Gly

```
                130                 135                 140
Asn Phe Pro Gly Trp Lys Gly Phe Tyr Lys Pro Thr Gly Ser Gly Trp
145                 150                 155                 160

Val His Ala Arg Lys Ala Met Lys Ala Ala Phe Glu Glu Ser Glu Arg
                165                 170                 175

Leu Gly Val Lys Phe Ile Thr Gly Ser Pro Glu Gly Lys Val Glu Ser
                180                 185                 190

Leu Ile Phe Glu Asp Gly Asp Val Arg Gly Ala Lys Thr Ala Asp Gly
                195                 200                 205

Lys Glu His Arg Ala Asp Arg Thr Ile Leu Ser Ala Gly Ala Ser Ala
210                 215                 220

Glu Phe Phe Leu Asp Phe Glu Asn Gln Ile Gln Pro Thr Ala Trp Thr
225                 230                 235                 240

Leu Gly His Ile Gln Met Thr Pro Glu Glu Thr Lys Leu Tyr Lys Asn
                245                 250                 255

Leu Pro Pro Leu Phe Asn Ile Asn Gln Gly Phe Phe Met Glu Pro Asp
                260                 265                 270

Glu Asp Leu His Gln Leu Lys Met Cys Asp Glu His Pro Gly Tyr Cys
                275                 280                 285

Asn Trp Val Glu Lys Pro Gly Ser Lys Tyr Pro Gln Ser Ile Pro Phe
290                 295                 300

Ala Lys His Gln Val Pro Thr Glu Ala Glu Arg Arg Met Lys Gln Phe
305                 310                 315                 320

Leu Lys Asp Ile Met Pro Gln Leu Ala Asp Arg Pro Leu Val His Ala
                325                 330                 335

Arg Ile Cys Trp Cys Ala Asp Thr Gln Asp Arg Met Phe Leu Ile Thr
                340                 345                 350

Tyr His Pro Arg His Pro Ser Leu Val Ile Ala Ser Gly Asp Cys Gly
                355                 360                 365

Thr Gly Tyr Trp His Ile Thr Ser Ile Gly Lys Phe Ile Ser Asp Cys
                370                 375                 380

Met Glu Gly Thr Leu Glu Glu Arg Phe Ala Lys Phe Trp Arg Trp Arg
385                 390                 395                 400

Pro Glu Lys Phe Thr Glu Phe Trp Gly Lys Asp Pro Leu Asp Arg Phe
                405                 410                 415

Gly Ala Asp Asp Lys Ile Met Asp Leu Pro Lys Ser Asp Val Glu Gly
                420                 425                 430

Trp Thr Asn Ile Lys Asn Asp Ile
                435                 440

<210> SEQ ID NO 9
<211> LENGTH: 440
<212> TYPE: PRT
<213> ORGANISM: Artificial Sequence
<220> FEATURE:
<223> OTHER INFORMATION: Synthetic protein sequence of SEQ ID NO: 3
<220> FEATURE:
<221> NAME/KEY: MUTAGEN
<222> LOCATION: (372)..(372)

<400> SEQUENCE: 9

Ala Ser Thr Leu Thr Lys Gln Ser Gln Ile Leu Ile Val Gly Gly Gly
1               5                   10                  15

Thr Trp Gly Cys Ser Thr Ala Leu His Leu Ala Arg Arg Gly Tyr Thr
                20                  25                  30

Asn Val Thr Val Leu Asp Val Asn Arg Ile Pro Ser Pro Ile Ser Ala
```

-continued

```
              35                  40                  45
Gly His Asp Val Asn Lys Leu Ala Gly Arg Leu Ser Thr Ala Asp Ser
         50                  55                  60

Lys Gly Asp Asp Glu Asp Ser Ile Trp Lys Ala Leu Ser Tyr Ala Ala
 65                  70                  75                  80

Ala Gln Gly Trp Leu His Asp Pro Val Phe Gln Pro Phe Cys His Asn
                 85                  90                  95

Thr Gly Ser Val Val Ala Gly Ser Thr Pro Lys Ser Ile Lys Gln Leu
                100                 105                 110

Val Glu Asp Glu Ile Gly Asp Asp Ile Asp Gln Tyr Thr Pro Leu Asn
            115                 120                 125

Thr Ala Glu Asp Phe Arg Lys Thr Met Pro Glu Gly Ile Leu Thr Gly
        130                 135                 140

Asn Phe Pro Gly Trp Lys Gly Phe Tyr Lys Pro Thr Gly Ser Gly Trp
145                 150                 155                 160

Val His Ala Arg Lys Ala Met Lys Ala Ala Phe Glu Glu Ser Glu Arg
                165                 170                 175

Leu Gly Val Lys Phe Ile Thr Gly Ser Pro Glu Gly Lys Val Glu Ser
                180                 185                 190

Leu Ile Phe Glu Asp Gly Asp Val Arg Gly Ala Lys Thr Ala Asp Gly
            195                 200                 205

Lys Glu His Arg Ala Asp Arg Thr Ile Leu Ser Ala Gly Ala Ser Ala
        210                 215                 220

Glu Phe Phe Leu Asp Phe Glu Asn Gln Ile Gln Pro Thr Ala Trp Thr
225                 230                 235                 240

Leu Gly His Ile Gln Met Thr Pro Glu Glu Thr Lys Leu Tyr Lys Asn
                245                 250                 255

Leu Pro Pro Leu Phe Asn Ile Asn Gln Gly Phe Phe Met Glu Pro Asp
            260                 265                 270

Glu Asp Leu His Gln Leu Lys Met Cys Asp Glu His Pro Gly Tyr Cys
        275                 280                 285

Asn Trp Val Glu Lys Pro Gly Ser Lys Tyr Pro Gln Ser Ile Pro Phe
290                 295                 300

Ala Lys His Gln Val Pro Thr Glu Ala Glu Arg Arg Met Lys Gln Phe
305                 310                 315                 320

Leu Lys Asp Ile Met Pro Gln Leu Ala Asp Arg Pro Leu Val His Ala
                325                 330                 335

Arg Ile Cys Trp Cys Ala Asp Thr Gln Asp Arg Met Phe Leu Ile Thr
            340                 345                 350

Tyr His Pro Arg His Pro Ser Leu Val Ile Ala Ser Gly Asp Cys Gly
        355                 360                 365

Thr Gly Tyr Met His Ile Thr Ser Ile Gly Lys Phe Ile Ser Asp Cys
    370                 375                 380

Met Glu Gly Thr Leu Glu Glu Arg Phe Ala Lys Phe Trp Arg Trp Arg
385                 390                 395                 400

Pro Glu Lys Phe Thr Glu Phe Trp Gly Lys Asp Pro Leu Asp Arg Phe
                405                 410                 415

Gly Ala Asp Asp Lys Ile Met Asp Leu Pro Lys Ser Asp Val Glu Gly
            420                 425                 430

Trp Thr Asn Ile Lys Asn Asp Ile
        435                 440

<210> SEQ ID NO 10
```

-continued

```
<211> LENGTH: 440
<212> TYPE: PRT
<213> ORGANISM: Artificial Sequence
<220> FEATURE:
<223> OTHER INFORMATION: Synthetic protein sequence of SEQ ID NO: 4
<220> FEATURE:
<221> NAME/KEY: MUTAGEN
<222> LOCATION: (372)..(372)

<400> SEQUENCE: 10
```

```
Ala Ser Thr Leu Thr Lys Gln Ser Gln Ile Leu Ile Val Gly Gly
1               5                   10                  15

Thr Trp Gly Cys Ser Thr Ala Leu His Leu Ala Arg Arg Gly Tyr Thr
            20                  25                  30

Asn Val Thr Val Leu Asp Val Asn Arg Ile Pro Ser Pro Ile Ser Ala
                35                  40                  45

Gly His Asp Val Asn Lys Leu Ala Gly Arg Leu Ser Thr Ala Asp Ser
        50                  55                  60

Lys Gly Asp Asp Glu Asp Ser Ile Trp Lys Ala Leu Ser Tyr Ala Ala
65                  70                  75                  80

Ala Gln Gly Trp Leu His Asp Pro Val Phe Gln Pro Phe Cys His Asn
                85                  90                  95

Thr Gly Ser Val Val Ala Gly Ser Thr Pro Lys Ser Ile Lys Gln Leu
            100                 105                 110

Val Glu Asp Glu Ile Gly Asp Ile Asp Gln Tyr Thr Pro Leu Asn
        115                 120                 125

Thr Ala Glu Asp Phe Arg Lys Thr Met Pro Glu Gly Ile Leu Thr Gly
130                 135                 140

Asn Phe Pro Gly Trp Lys Gly Phe Tyr Lys Pro Thr Gly Ser Gly Trp
145                 150                 155                 160

Val His Ala Arg Lys Ala Met Lys Ala Ala Phe Glu Glu Ser Glu Arg
                165                 170                 175

Leu Gly Val Lys Phe Ile Thr Gly Ser Pro Glu Gly Lys Val Glu Ser
            180                 185                 190

Leu Ile Phe Glu Asp Gly Asp Val Arg Gly Ala Lys Thr Ala Asp Gly
        195                 200                 205

Lys Glu His Arg Ala Asp Arg Thr Ile Leu Ser Ala Gly Ala Ser Ala
210                 215                 220

Glu Phe Phe Leu Asp Phe Glu Asn Gln Ile Gln Pro Thr Ala Trp Thr
225                 230                 235                 240

Leu Gly His Ile Gln Met Thr Pro Glu Glu Thr Lys Leu Tyr Lys Asn
                245                 250                 255

Leu Pro Pro Leu Phe Asn Ile Asn Gln Gly Phe Phe Met Glu Pro Asp
            260                 265                 270

Glu Asp Leu His Gln Leu Lys Met Cys Asp Glu His Pro Gly Tyr Cys
        275                 280                 285

Asn Trp Val Glu Lys Pro Gly Ser Lys Tyr Pro Gln Ser Ile Pro Phe
290                 295                 300

Ala Lys His Gln Val Pro Thr Glu Ala Glu Arg Arg Met Lys Gln Phe
305                 310                 315                 320

Leu Lys Asp Ile Met Pro Gln Leu Ala Asp Arg Pro Leu Val His Ala
                325                 330                 335

Arg Ile Cys Trp Cys Ala Asp Thr Gln Asp Arg Met Phe Leu Ile Thr
            340                 345                 350

Tyr His Pro Arg His Pro Ser Leu Val Ile Ala Ser Gly Asp Cys Gly
        355                 360                 365
```

-continued

```
Thr Gly Tyr Val His Ile Thr Ser Ile Gly Lys Phe Ile Ser Asp Cys
        370             375             380

Met Glu Gly Thr Leu Glu Glu Arg Phe Ala Lys Phe Trp Arg Trp Arg
385             390             395                     400

Pro Glu Lys Phe Thr Glu Phe Trp Gly Lys Asp Pro Leu Asp Arg Phe
                405             410             415

Gly Ala Asp Asp Lys Ile Met Asp Leu Pro Lys Ser Asp Val Glu Gly
            420             425             430

Trp Thr Asn Ile Lys Asn Asp Ile
        435             440
```

COMPOSITION FOR ASSAYING GLYCOPROTEIN

This application is the national phase under 35 U.S.C. § 371 of PCT International Application No. PCT/JP02/00721 which has an International filing date of Jan. 30, 2002, which designated the United States of America.

TECHNICAL FIELD

The present invention relates to a composition for assaying glycated proteins and a method for assaying glycated proteins. The composition and method for assaying glycated proteins of the present invention can be used in clinical examinations and can precisely assay glycated proteins.

BACKGROUND ART

Assaying glycated proteins is very important in diagnosing and controlling diabetes. Glycated hemoglobin (GHb) that reflects an average blood glucose value in the past about 1 to 2 months, glycated albumin (GA) that reflects an average blood glucose value in the past about two weeks, fructosamine (FRA) which generally indicates glycated proteins exhibiting reduction capability in blood serum, and the like are measured every day. GHb is a glycated product of hemoglobin, i.e., the α-amino group of N-terminal valine on the β-chain of hemoglobin is glycated. GA and FRA are glycated products of albumin and blood serum protein respectively, i.e. the ε-amino group on a lysine residue of albumin or blood serum protein is glycated.

An enzymatic method is given as a simple, easy, and inexpensive method for accurately assaying glycated proteins. Japanese Patent Applications Laid-open No. 6-46846, No. 5-192193, No. 2-195900, and No. 2-195899, and International Patent Application Publication Number WO 98/48043, and WO 97/13872 are given as examples of documents disclosing the enzymatic method.

However, to provide a composition for precisely assaying glycated proteins, it is essential 1) to avoid the effect of globulin components and ascorbic acid and 2) to stabilize protease, at least the enzyme that reacts with glycated amino acids. In addition, in the case where the glycated protein is a glycated albumin, it is important 3) to precisely assay albumin and 4) to avoid the effect of glycated hemoglobin.

1) Conventional Methods for Avoiding the Effect of Globulin Components and Ascorbic Acid It is known that the amount of globulin proteins of a diabetic changes and affects the value of FRA [Rodrigues, S. et al., Clin. Chem. 35: 134-138 (1989)]. The present inventors have developed a method of selectively inhibiting the action of a protease on globulin components by adding a specific metal ion and a protein A or G to a protease reaction solution (Japanese Patent Application No. 11-231259). Glycated proteins can be assayed without being affected by globulin components using this method of the present invention. As a globulin-selective protease inhibitor used in the method, metals, protein A, and protein G are mentioned. Among the metals specified in this patent application, highly effective metals are heavy metals that may have environmental safety problems. Less effective metals may make a reagent solution turbid if combined with other reagents (or compositions). In addition, protein A and protein G are very expensive reagents.

As a method for selectively adsorbing globulin in blood, a blood-treating agent adsorbing endotoxins and globulin in blood utilizing the principle of chromatography and a vinyl copolymer introduced a ligand having a steroid skeleton is known (Japanese Patent Application Laid-open No. 61-94663). However, the results shown in Table 1 of Examples of Japanese Patent Application Laid-open No. 61-94663 indicate that only α1-globulin and α2-globulin have been confirmed to be adsorbed, but γ-globulin that makes up 70% or more of globulin components was not adsorbed. Supposing that γ-globulin was adsorbed, the capability of the blood-treating agent of inhibiting protease activity on γ-globulin cannot be anticipated.

Occasions of a large amount of ascorbic acid intake as a supplement are increasing in recent years. Clinical samples containing ascorbic acid at a high concentration are also increasing. Ascorbic acid induces a variety of effects on clinical examinations due to the strong reducing action.

As a method for obviating the effects of ascorbic acid, a method of eliminating the ascorbic acid in samples chemically or enzymatically using an ascorbic acid oxidase has been known. When glycated amino acids produced by fragmenting glycated proteins with a protease are assayed using an enzyme which reacts at least with a glycated amino acid, a method of previously eliminating ascorbic acid using an ascorbic acid oxidase (ASOx) at the time of reaction with a protease is preferable in view of a small effect on the coloring system.

As an example of eliminating ascorbic acid in samples using ASOx in the presence of a protease, an experiment of reacting ASOx with a sample solution in a 2-[4-(2-hydroxyethyl)-1-piperazinyl]ethane sulfonic acid (HEPES) buffer solution at pH 8.0 has been reported (Clinical Chemistry, 27: 99-106, 1998). The report describes that the ascorbic acid treating capability did not change after cold storage for two weeks.

However, the investigation made by the present inventors has revealed that when a HEPES buffer solution at pH 8.0, a protease, and ASOx are present, the ascorbic acid treating capability has been lost almost entirely in one day when stored at 37° C. or in two weeks when stored at 10° C.

2) Prior Art for Stabilizing Proteases and Enzymes Reacting at Least with a Glycated Amino Acid A solution of protease at an inconceivably high concentration of a level which cannot be seen in another field such as the food industry is used in clinical assay of glycated proteins. Proteases are known to self-digest in an aqueous solution. It is difficult to assume that a protease remains stable in an aqueous solution at such a high concentration. Therefore, proteases used for a composition for assaying glycated proteins have been supplied as a freeze dry product.

There has been no composition for assaying glycated proteins nor a method of assaying glycated proteins in which a protease is stabilized in a liquid state storable for a long period of time. There has also been no composition for assaying glycated proteins nor a method of assaying glycated proteins in which the enzyme reacting at least with a glycated amino acid was stabilized in a liquid state storable for a long period of time.

3) Prior Art Relating to a Method for Precisely Assaying Albumin

Anti-albumin antibody immunization and a dying method using bromocresol green (BCG), bromocresol purple (BCP), or the like are given as the method for assaying albumin. The dying method is widely used in everyday inspections due to the simple procedure and low cost. Although the effect of BCG on globulin component has been confirmed, BCG has disadvantages of low specificity to albumin.

On the other hand, BCP is easily affected by coexisting substances in spite of the high specificity to albumin. In particular, BCP is affected by SH compounds giving rise to a problem of variation in the assay results according to oxidation-reduction conditions of albumin. As a means for solving this problem, a method of reacting BCP in the presence of a protein denaturing agent and/or an SH reagent has been proposed (Japanese Patent Application Laid-open No. 10-232233) However, there have been no examples on the study of the reactivity of BCP to GA and non-glycated albumin (NGA).

4) Prior Art for Avoiding the Effect of Glycated Hemoglobin

As mentioned above, GA is derived from albumin by glycation of the ε-amino group, whereas GHb is obtained by glycating α-amino group of N-terminal valine on the β-chain of hemoglobin. Therefore, in case GA is applied as measuring object it is desirable to determine only amino acids in which the ε-amino group has been glycated.

Although several enzymes exhibiting high specificity to ε-amino group but no action on glycated valine has been known (Japanese Patent Application Laid-open No. 11-243950), none of them are supplied at a sufficiently low cost for the enzymes to be used in practice. Of these enzymes, a fructosyl amino acid oxidase (FOD) derived from *Fusarium oxysporm* possesses high reactivity and is useful. The inventors have reported separately the gene of FOD (Japanese Patent Application Laid-open No. 10-201473). Although the process using the gene exhibits high productivity and can produce FOD at a low cost, the reactivity with glycated valine of which the α amino group has been glycated confirmed by the inventors does not exhibit satisfactory specificity.

DISCLOSURE OF THE INVENTION

An object of the present invention is to provide, in precisely assaying glycated proteins, a composition in which 1) the effect of globulin components and ascorbic acid can be avoided and 2) proteases and enzymes that react at least with a glycated amino acid are stabilized, and to provide a stabilizing method. Another object of the present invention is to provide, in the case where the glycated protein is a glycated albumin, a composition that 3) can precisely assay albumin and 4) can avoid the effect of glycated hemoglobin, and to provide a method for avoiding the effect of the glycated hemoglobin.

For precisely assaying glycated proteins, it is essential 1) to avoid the effect of globulin components and ascorbic acid and 2) to stabilize proteases and enzymes that react at least with a glycated amino acid. In addition, when the glycated protein is a glycated albumin, it is essential 3) to precisely assay albumin and 4) to avoid the effect of glycated hemoglobin.

1) Method for Avoiding the Effect of Globulin Components and Ascorbic Acid

The inventors of the present invention have conducted extensive studies and have found that if one or more members selected from the group consisting of deoxycholic acid, deoxycholic acid amide, cholic acid amide, a quaternary ammonium salt, a quaternary ammonium salt-type cationic surfactant, concanavalin A, octyl glucoside, and betaine are added to a protease reaction solution, the effect of a protease on globulin components can be selectively inhibited, and that if an enzyme reacting at least with a glycated amino acid is directly reacted with this reaction solution, glycated proteins can be precisely assayed in a simple manner and with an excellent reproducibility without inhibition of the enzymatic effect. These compounds are economically advantageous, have no environmental and safety problems as compared with the methods using conventional technologies, and do not produce turbidity when mixed with samples.

ASOx can efficiently remove ascorbic acid. However, it is usually difficult to assume that ASOx is stable in a reaction solution containing a large amount of proteases. In fact, according to the investigation made by the inventors of the present invention relating to the types of proteases, protease inhibitors, and types of ASOx, no conditions under which the ASOx is stable in a reaction solution containing a large amount of proteases have been discovered.

However, as a result of dedicated investigations, the present inventors have surprisingly found that the stability of ASOx significantly increases according to the types of buffering solutions.

2) Stabilization of Proteases and Enzymes Reacting at Least with a Glycated Amino Acid.

As mentioned above, a solution of a protease is used at a high protease concentration in clinical assay of glycated proteins. The protease itself becomes principally unstable in such a solution. However, as a result of extensive studies, the present inventors have found that stability of proteases significantly increases and the proteases can be stored in a high concentration solution for a long period of time if dimethylsulfoxide, alcohol, water-soluble calcium salt, sodium chloride, a quaternary ammonium salt, or a quaternary ammonium salt-type cationic surfactant is added.

Enzymes reacting at least with a glycated amino acid are not stable because the activity of the enzymes decreases to about 10% of the original activity if stored in a liquid state for four days at 37° C. However, as a result of extensive studies, the present inventors have found that if a stabilizer selected from the group consisting of sugar alcohol, sucrose, water-soluble magnesium salt, water-soluble calcium salt, ammonium sulfate, amino acid, and sarcosine is added to an enzyme reacting at least with a glycated amino acid, a surprisingly high stabilization effect to a degree that almost no decrease in the activity is seen when stored in a liquid state for four days at 37° C. can be obtained.

In addition, although a protease exhibits a high proteolytic activity at near the optimum pH, an autodigestion reaction of the protease proceeds at the same time, making it difficult to store the protease particularly in a liquid state. However, as a result of extensive studies, the present inventors have found that proteases can be stored in a stable manner without being affected by the conditions during assay by providing a first reagent formulated to appropriately induce a reaction of the proteases and a second reagent formulated to stabilize the proteases in a liquid state. The inventors have further found that precise assay is possible without affection to the measurement even if an enzyme to be used for a preliminary reaction is incorporated in the second reagent. In addition, if an enzyme reacting at least with a glycated amino acid is added to the first reagent, the glycated amino acid in a sample can be previously eliminated and glycated proteins can be selectively assayed.

3) Method for Precisely Assaying Albumin

Investigations by the present inventors have revealed unexpectedly that the reactivity of BPC with GA differs from the reactivity of BPC with NGA and that if a large amount of NGA is present, the analytical value is negatively affected. As a result of extensive studies, the inventors have found that albumin in a sample containing a large amount of NGA can be precisely assayed by treating the sample with a protein denaturing agent and/or a compound having an S—S bond prior to or simultaneously with assaying albumin.

4) Avoiding the Effect of Glycated Hemoglobin

As a result of extensive studies on the above problems, the present inventors have prepared a mutant FOD by modifying an FOD gene originating from *Fusarium oxysporm* IFO-9972 strain and determined the properties of the mutant FOD to discover that the substrate specificity remarkably changes by replacing the 372nd lysine from the N-terminal with another amino acid. Furthermore, the inventors have prepared several modified FODs that exhibit only an extremely low reactivity with glycated valine and almost specifically react with glycated lysine.

These mutant FODs that have been discovered based on the above findings have lost the reactivity with glycated valine by replacing the 372nd lysine in the amino acid sequence in the Sequence ID No. 1 with another amino acid. Specifically, these are mutant FODs of claim 1 that are obtained by replacing the 372nd lysine in the amino acid sequence in the Sequence ID No. 1 with tryptophan, methionine, or valine.

Finally, the inventors of the present invention have completed a composition and a method for precisely assaying glycated proteins by putting the above findings together.

The constitution and preferred embodiment of the present invention will be described in more detail below.

Any proteases can be used in the present invention inasmuch as the proteases can effectively react with glycated proteins contained in samples and effectively produce glycated amino acids and/or glycated peptides originating from the glycated proteins. Examples include proteases originating from animals, plants, and microorganisms such as *Bacillus, Aspergillus, Penicillium, Streptomyces, Staphylococcus, Clostridium, Lysobacter, Glifila*, Yeast, *Tritirachium, Thermus, Pseudomonus*, and *Achromobacter*, and the like.

When the glycated protein to be assayed is GA, proteases originating from microorganisms belonging to genus *Bacillus* or *Streptomyces* are preferable due to the high reactivity to human albumin (Alb). When the glycated protein to be assayed is GHb, proteases originating from microorganisms belonging to genus *Bacillus, Aspergillus, Streptomyces*, or *Tritirachium* are preferable due to the high reactivity to human hemoglobin (Hb).

The protease activity can be measured in the present invention as follows.

<<Method for Measuring Protease Activity>>

The activity of a protease exhibiting color change corresponding to 1 μg of thyrosin in one minute at 30° C. under the following conditions is indicated as 1 PU (proteolytic unit).

| <Substrate> | 0.6% milk casein (manufactured by Merck & Co., Inc.) |
|---|---|
| <Enzyme solution> | diluted to 10–20 PU |
| <Enzyme diluting solution> | 20 mM acetic acid buffer solution (pH 7.5), 1 mM calcium acetate, 100 mM sodium chloride |
| <Reaction termination solution> | 0.11 M trichloroacetic acid, 0.22 M sodium acetate, 0.33 M acetic acid |

<Procedure>

A protease solution is dissolved in an enzyme diluting solution to make a concentration of 10-20 PU/ml. 1 ml of this solution is charged in a test tube and heated to 30° C. 5 ml of a substrate solution previously heated to 30° C. is added. Exactly 10 minutes thereafter 5 ml of a reaction termination solution is added to terminate the reaction. The mixture is heated at 30° C. for 30 minutes to cause precipitate to deposit. The mixture is filtered through a Toyo filter No. 131 (9 cm) to obtain a filtrate. For blank assay, 1 ml of the protease solution is heated at 30° C. in a test tube, 5 ml of the reaction termination solution is added, then 5 ml of the substrate solution is added, following which the precipitate is deposited and filtered in the same manner. 5 ml of 0.55 M sodium carbonate solution and 1 ml of Folin reagent diluted 3-fold are added to 2 ml of the filtrate. After the reaction at 30° C. for 30 minutes, the absorbance at 660 nm is measured. The absorbance change is determined by subtracting the absorbance of the blank from the absorbance of the sample reacted with the enzyme. The enzyme activity is then determined using a separately prepared standard activity curve.

<Preparation of Standard Activity Curve>

An enzyme solution adjusted to a concentration of about 50 PU/ml is diluted to prepare several enzyme solutions with a series of dilution magnification at a concentration of 2-50 PU/ml. The above procedure is applied to each enzyme solution. The resulting absorbance change is plotted along the vertical axis and the dilution magnification is plotted along the horizontal axis. On the other hand, a standard thyrosin solution (a thyrosin concentration: 9.09 μg/ml) is prepared by dissolving L-thyrosin in 0.2 N hydrochloric solution to make a concentration of 0.01% and adding 10 ml of 0.2 N hydrochloric solution to 1 ml of the L-thyrosin solution. The above measuring procedure is applied to 2 ml of the standard thyrosin solution and 2 ml of 0.2 N hydrochloric solution. The resulting absorbance change corresponds to 18.2 μg of thyrosin. The absorbance change is plotted on the above graph. The intersecting point of a vertical line drawn from the plotted point and the horizontal axis corresponds to 10 PU/ml.

These proteases may be used in any concentration at which the target proteins can be efficiently digested in a specified period of time, usually in the range of 1-100,000 PU/ml, and preferably 10-10,000 PU/ml, for example.

As the enzyme capable of reacting at least with a glycated amino acid that can be used in the present invention, any enzymes that can effectively react with a glycated amino acid or a glycated peptide produced from a glycated protein contained in a sample solution and can substantially assay the glycated protein by the effect of proteases may be used. For example, an enzyme reacting at least with a g glycated amino acid, which effectively reacts with amino acids in which the α-amino group is glycated, an enzyme reacting at least with a glycated amino acid, which effectively reacts with amino acids in which the ε-amino group is glycated, and the like can be given.

As examples of the enzyme reacting at least with a glycated amino acid, which effectively reacts with the amino acids in which the ε-amino group is glycated, FODs derived from microorganisms belonging to genus *Gibberella, Aspergillus, Candida, Penicillium, Fusarium, Acremonium*, or *Debaryomyces* can be given.

As examples of the enzyme reacting at least with a glycated amino acid, which effectively reacts with amino acids in which the α-amino group is glycated, enzymes derived from microorganisms belonging to genus *Corynebacterium* can be given.

In addition, as examples of the enzyme which has a sufficient activity in the presence of a protease and can be prepared at low cost, a ketoamine oxidase produced by gene recominiation (R-FOD, manufactured by Asahi Kasei Corporation) and a mutant type FOD (R-FOD-II, manufactured by Asahi Kasei Corporation) extremely decreased the reactivity with glycated valine can be given.

DNA encoding the FOD protein derived from *Fusarium oxysporum* IFO-9972 strain from which R-FOD-II is produced can be obtained by extracting chromosome DNA from the *Fusarium oxysporum* IFO-9972 strain by a conventional method and separating the DNA encoding the FOD protein by the PCR method or hybridization method.

To introduce a mutation into the obtained FOD gene, the PCR method or site-directed mutagenesis can be employed if the DNA is directly mutated. If incidental mutation is employed, either DNA-repair deficient *Escherichia coli* can be used as a host or a host microorganism with an FOD gene introduced into a medium containing a DNA mutation source may be cultured.

The mutant FOD gene obtained in this manner is introduced into a host microorganism using an appropriate host-vector system. A microorganism having a recombinant DNA plasmid containing the FOD gene is separated by screening using a marker for the expression vector and expression of the FOD activity or a DNA probe as an index. The mutant FOD can be obtained by culturing the gene recombinant microorganism, extracting recombinant protein from the microorganism, and purifying the protein.

A specific method for obtaining the mutant FOD is as follows. In the following procedure, the conventional method includes, for example, a method of Maniatis et al. (Maniatis, T., et al. Molecular Cloning. Cold Spring Harbor Laboratory 1982, 1989) or a method described in manuals attached to various commercially available enzymes and kits.

To introduce a mutant to the separated FOD gene, a PCR method using a 3'→5' repair-deficient polymerase such as a Taq polymerase under the conditions in which a manganese ion is added can be used. Alternatively, a method of introducing the FOD gene into a DNA repair-deficient *Escherichia coli* host, culturing the host microorganism in a medium containing a mutant source such as dianisidine to induce a gene mutation, and separating the mutant acquiring the target substrate specificity from the produced mutant candidate strains can be used.

The FOD mutation introduced using the above methods can be confirmed by determining the base sequence of the gene into which the mutant has been introduced by the dideoxy method (Sangar, F. (1981) Science, 214, 1205-1210).

Once the mutation has been determined, the specific mutation can also be introduced by the site-directed mutagenesis using the method of Zoller et al (Zoller, M. J. and Smith, M. (1983), Methods in Enzymology, 154, 367).

Mutation of the amino acid sequence of the polypeptide forming the mutant FOD can be determined from the base sequence of the mutant gene. The mutant FOD obtained by the above method can be produced as a recombinant by incorporating the mutant FOD gene into an appropriate host-vector system.

As the vector into which the mutant FOD gene is incorporated, vectors constructed for gene recombinant use from a phage or plasmid that can autonomously grow in a host microorganism are appropriate. As the phage vector, when a microorganism belonging to *E. coli* is used as a host microorganism, for example, λgt•λC, λgt•λB, and the like can be used. As the plasmid vector, when *E. coli* is used as a host microorganism, for example, plasmids pBR322, pBR325, pACYC184, pUC12, pUC13, pUC18, pUC19, pUC118, pIN I, and Bluescript KS+ are preferably used; when *Bacillus subtilis* is used as a host microorganism, pUB110 and pKH300PLK can be used; when *Actinomyces* is used as a host microorganism, pIJ680 and pIJ702 can be used; and when Yeast, particularly *Saccharomyces cerevisiae*, is used as a host microorganism, Yrp7, pYC1, and Yep3 can be used.

To incorporate a mutant FOD gene into the vector thus obtained, both the vector and the mutant FOD gene are digested with an appropriate restriction endonuclease that can produce the same terminals and DNA fragments containing the mutant FOD gene and vector fragments are combined using a DNA ligase according to a conventional method.

Any microorganisms can be used as the host microorganism into which the vector combined with the mutant FOD gene is transferred inasmuch as a recombinant DNA can stably and autonomously grow. When the host microorganism is a microorganism belonging to *E. coli*, for example, *E. coli* DH1, *E. coli* JM109, *E. coli* W3110, *E. coli* C600, and the like can be used. When the host microorganism is a microorganism belonging to *Bacillus subtilis, Bacillus subtilis* ISW1214 and the like can be used. When the host microorganism is a microorganism belonging to *Actinomyces, Streptomyces lividans* TK24 and the like can be used. When the host microorganism is a microorganism belonging to *Saccharomyces cerevisiae, Saccharomyces cerevisiae* INVSC1 and the like can be used.

As the method for incorporating the recombinant DNA into the host microorganism, when the host microorganism belongs to *E. coli, Saccharomyces cerevisiae*, or *Streptomyces lividans*, for example, the recombinant DNA can be transferred to the host microorganisms converted into competent cells according to a conventional method. Electroporation may be applied according to the type of the strain.

To produce a mutant FOD, a method of culturing the host microorganism into which the mutant FOD gene has been introduced in an appropriate medium, collecting the cultured cells, destroying the cells by ultrasonic pulverization in an appropriate buffer solution or by a lysozyme treatment to prepare the cell extract can be employed. It is possible to add a signal sequence to cause secretion expression, whereby the mutant FOD is accumulated in the culture broth.

The mutant FOD thus produced is separated and purified by conventional ammonium sulfate precipitation, gel filtration, column purification, and the like and supplied as an enzyme preparation.

The components are commonly used in the above gene manipulation technique in a proportion, for example, of about 1-10 U of the restriction endonuclease, about 300 U of ligase, and about 1-10 U of other enzymes for 0.1-10 μg of DNA and vector DNA from the source microorganism.

As specific examples of the transgenic microorganism containing the mutant FOD gene and capable of producing the mutant FOD, *Escherichia coli* JM109·pcmFOD3 (FERM BP-7847), a transgenic microorganism having a microorganism belonging to *Escherichia coli* as the host microorganism and possessing a plasmid pcmFOD3 that contains the mutant FOD gene therein, *Escherichia Coli* JM109·pcmFOD4, a transgenic microorganism possessing pcmFOD4, and *Escherichia coli* JM109·pcmFOD5 (FERM BP-7848), a transgenic microorganism possessing pcm-FOD5 can be given. The structures of these plasmids are shown in FIG. 7.

The *Escherichia coli* JM109·pcmFOD3 and *Escherichia coli* JM109·pcmFOD5 were deposited with the International Patent Organism Depositary, National Institute of Advanced Industrial Science and Technology, an Independent Administrative Institution (Central 6, 1-1-1 Higashi, Tsukuba-shi, Ibaraki, Japan) on Jan. 16, 2001, under the deposition No. FERM BP-7847 and No. FERM BP-7848, respectively.

In producing the mutant FOD from the transgenic microorganism, the transgenic microorganism is cultured in a nutritious medium to cause the mutant FOD to be produced in the cells or the culture broth, collecting the cells by filtration or centrifugation of the culture broth after the end of cultivation, destroying the cells by a mechanical means or enzymatic means using lysozyme or the like, optionally condensing the aqueous solution of the mutant FOD by adding EDTA and/or a suitable surfactant, and purifying the condensate or the non-condensed aqueous solution by ammonium sulfate fractionation, gel filtration, adsorption chromatography such as affinity chromatography, or ion exchange chromatography, thereby obtaining high purity mutant FOD.

Culture conditions for the transgenic microorganism are selected taking the nutritious and physiological properties of the microorganism into consideration. Usually, liquid culture conditions are employed in many cases. However, deep aerated agitation is advantageous for industrial production. As nutritious sources of the culture medium, nutritious sources commonly used in microbial incubation can be used.

Any utilizable hydrocarbon compounds such as glucose, sucrose, lactose, maltose, fructose, and molasses can be used as a carbon source. Any utilizable nitrogen compounds such as peptone, meat extract, yeast extract, and casein hydrolysate can be used as a nitrogen source.

Other components including salts such as a phosphate, carbonate, sulfate, magnesium salt, calcium salt, potassium salt, iron salt, manganese salt, and zinc salt, specific amino acids, and specific vitamins are added, if necessary.

The culture temperature may be appropriately varied in the range within which the microorganism can grow and produce the mutant FOD. In the case of *E. coli*, the preferable temperature range is about 20-42° C. Although the culture time may be somewhat varied according to the culture conditions, the culture may be terminated at an appropriate time when the yield of mutant FOD reaches maximum. In the case of *E. coli*, the culture time is usually 12-48 hours. The pH of the culture medium may be appropriately varied in the range within which the microorganism can grow and produce the mutant FOD. In the case of *E. coli*, the preferable pH range is about pH 6-8.

Mutant FOD in the culture medium can be utilized by collecting the culture medium containing the cells as is. Usually, however, when the mutant FOD is contained in the culture broth, a solution containing the mutant FOD separated from the microorganism cells by filtration or centrifugation is used. When the mutant FOD is included in the cells, cells are collected from the resulting culture broth by filtration, centrifugation, or other means, the collected cells are optionally destroyed by a mechanical means or an enzymatic means using lysozyme or the like, and the mutant FOD is dissolved in water after adding a chelating agent such as EDTA and/or a surfactant to select and collect the mutant FOD as an aqueous solution.

The solution containing the mutant FOD thus obtained is condensed under reduced pressure or by filtering through a membrane, further the mutant FOD is precipitated by fractional precipitation by a salting out treatment using ammonium sulfate, sodium sulfate, or the like.

The precipitate is then dissolved in water and dialyzed through a semipermeable membrane to remove low molecular weight impurities. Alternatively, the solution containing the mutant FOD may be purified by gel filtration using an adsorbent, a gel filtration agent, or the like, adsorption chromatography such as affinity chromatography, or ion exchange chromatography. The mutant FOD-containing solution obtained by these means is concentrated under reduced pressure, freeze dried, or otherwise processed to provide purified mutant FOD.

Activity of enzyme reacting with glycated amino acid was measured using the following method.

<<Method for Measuring Activity of Enzyme Reacting with Glycated Amino Acid>>

<Composition of Reaction Solution>

| | |
|---|---|
| 50 mM | Tris buffer (pH 7.5) |
| 0.03% | 4-Aminoantipyrine (4-AA) (manufactured by Wako Pure Chemical Industries, Ltd.) |
| 0.02% | Phenol (manufactured by Wako Pure Chemical Industries, Ltd.) |
| 4.5 U/ml | Peroxidase (POD) (manufactured by Sigma-Aldrich Co.) |
| 1.0 mM | α-carbobenzoxy-ϵ-D-1-deoxy-fructosyl lysine or 1-deoxy-fructosyl valine (synthesized and purified according to the method by Hashiba et al. (Hashiba, H. et al., J. Agric. Food Chem., 24; 70, 1976. Hereinafter abbreviated respectively as "ZFL" and "FV") |

1 ml of the above reaction solution is placed in a small test tube and preheated at 37° C. for 5 minutes, then 0.02 ml of an appropriately diluted enzyme solution is added. The mixture is stirred to initiate the reaction. After the reaction for exactly 10 minutes, 2 ml of 0.5% SDS is added to terminate the reaction. Absorbance (As) at a wavelength of 500 nm is measured. As a blank test, the same procedure is followed using 0.02 ml of distilled water instead of the enzyme solution to measure the absorbance (Ab). The enzyme activity is determined from the difference (As-Ab) between the absorbance (As) after the enzyme reaction and the blank test absorbance (Ab). The correlation between the absorbance and produced hydrogen peroxide is previously determined using a standard solution of hydrogen peroxide. The amount of enzyme that can produce 1 μmol of hydrogen peroxide at 37° C. in one minute is defined as 1 U. The calculation formula is shown below.

Enzyme activity (U/ml)=$[(As-Ab)/12.0] \times [3.02/0.02] \times [1/10] \times [2/B]$ 3.02: Total reaction solution (ml)

0.02: Total enzyme solution (ml)

10: Reaction time

2: A coefficient indicating production of one molecule of a coloring matter in which 4-AA and phenol are condensed from two hydrogen peroxide molecules 12.0: Absorbance coefficient (mM) 4-AA-phenol B: Dilution magnification of the enzyme solution Among the mutant FODs obtained by the above method, the mutant FOD in which the 372nd lysine in the amino acid sequence in the Sequence ID No. 1 is replaced with tryptophan has the following enzymatic properties.

(1) Substrate Specificity

| ZFL | 100% |
|---|---|
| FV | 0% |

(2) Enzyme Reaction

The enzyme catalyzes the reaction of at least decomposing an amadori compound of α-amino acid or ε-amino acid to produce glucosone, hydrogen peroxide, and corresponding α-amino acid or ε-amino acid as shown in the following reaction formula.

1-deoxy-fructosyl amino acid +

$O_2 \rightleftarrows$ Glucosone + L-amino acid + $H_2O_2$ (3) Molecular Weight

The molecular weight of the enzyme determined by the column gel permeation method using a Sephadex G-100 and an eluate of 0.1 M phosphate buffer (pH 7.0) containing 0.2 M NaCl was 48,000±2,000. The results obtained using SDS-PAGE was 47,000±2,000.

(4) Isoelectric Point

The isoelectric point determined by fractionating the enzyme after applying a constant voltage of 700 V for 40 hours at 4° C. in a focusing electrophoresis using carrier ampholyte, followed by measuring the enzyme activity of each fraction, was pH 4.3±0.2.

(5) Km Value

The Km value to a synthetic substrate ZFL determined while changing the concentration of ZFL in a reaction solution containing 50 mM Tris-HCl buffer solution (pH 7.5), 0.03% 4-AA, 0.02% phenol, and 4.5 U/ml peroxidase was 3.4 mM.

(6) Optimum pH

The Enzyme activity was measured according to the above method for determining the enzyme activity, except that 100 mM acetate buffer solution (pH 4.4-5.4), phosphate buffer solution (pH 5.6-7.9), Tris-HCl buffer solution (pH 7.3-8.5), or glycine-sodium hydroxide buffer solution (pH 8.0-10.3) was used for the reaction solution instead of the 50 mM Tris-HCl buffer solution (pH 7.5). As a result, the enzyme exhibited the maximum activity at pH 7.5.

(7) pH Stability 0.5 ml of various buffer solutions containing 0.5 U of the enzyme, each used for the determination of the optimum pH at a concentration of 0.5 M, were incubated at 40° C. for 10 minutes, and these residual activities were then determined according to the activity measuring method described below. As a result, the enzyme was found to maintain 80% or more activity at pH 7.0-9.0.

(8) Heat Stability

A 0.5 U enzyme solution was prepared using 0.2 M Tris-HCl buffer solution (pH 7.5) and heated for 10 minutes, and the residual activity was determined according to the activity measuring method. As a result, the enzyme was found to maintain 95% or more activity up to 40° C.

(9) Optimum Temperature

The enzyme was reacted according to the activity measurement method using a 40 mM Tris-HCl buffer solution (pH 7.5) at different temperatures. After the reaction for 10 minutes, 2 ml of 0.5% sodium lauryl sulfate (hereinafter referred to as "SDS") was added to terminate the reaction. Absorbance (As) at a wavelength of 500 nm was measured. As a result, the enzyme exhibited the maximum activity at 50° C.

Next, a method for measuring glycated valine in a sample using an FOD having a reactivity with glycated valine after eliminating glycated lysine in the sample solution using a mutant FOD with a remarkably reduced reactivity with the glycated valine obtained by replacing the 372nd lysine in the amino acid sequence in the Sequence ID No. 1 with another amino acid, will be discussed.

Any FOD having no reactivity with glycated valine can be used to eliminate glycated lysine in a sample solution. For example, a mutant FOD with a remarkably reduced reactivity with glycated valine obtained by replacing the 372nd lysine in the amino acid sequence in the Sequence ID No. 1 with another amino acid is used. Among the mutant FODs, mutant FOD in which the 372nd lysine in the amino acid sequence in the Sequence ID No. 1 is replaced with any one of tryptophan, methionine, and valine is preferably used. The amount of the enzyme added to the reaction solution may be an amount sufficient to eliminate the glycated lysine in the sample solution, for example, 0.5-200 U/ml, and more preferably 1-50 U/ml.

There are no limitations to the FOD for measuring glycated valine inasmuch as the FOD can react with the glycated valine. For example, FOD originating from *Fusarium oxysporm* IFO-9972 strain can be used. The amount of the enzyme added to the reaction solution may be an amount sufficient to measure the glycated valine in the sample solution, for example, 0.5-200 U/ml, and more preferably 1-50 U/ml.

A specific measuring method comprises reacting glycated lysine in a sample solution containing the glycated lysine and glycated valine with mutant FOD in a first reaction, decomposing hydrogen peroxide produced in the reaction with catalase or the like, reacting hydrogen peroxide which was produced by reacting the glycated valine in the sample solution with FOD in a second reaction, with 4-aminoantipyrine (4-AA) and Trinder reagent, and calorimetrically measuring the produced color. Sodium azide that is a catalase inhibitor may be added to the second reaction solution.

As the protease inhibitor having selectivity with globulin components that can be used for precisely assaying glycated proteins according to the present invention, any inhibitor having selectivity with globulin components can be used inasmuch as such a inhibitor can mainly digest proteins other than the globulin components when the sample solution is reacted with a protease in the presence of the protease inhibitor having selectivity with globulin components. As preferable examples, deoxycholic acid, deoxycholic acid amide, cholic acid amide, quaternary ammonium salt, quaternary ammonium salt-type cationic surfactant, concanavalin A, octyl glucoside, and betaine can be given.

As deoxycholic acid amide, for example, N,N-Bis(3-D-gluconamidopropyl) deoxycholamido is preferable. As cholic acid amide, for example, 3-[(3-Cholamidopropyl) dimethylammonio]-2-hydroxypropane sulfonic acid, 3-[(3-Cholamidopropyl)dimethylammonio]propane sulfonic acid, N,N-Bis(3-D-gluconamido propyl) cholamido, or the like is preferable.

As quaternary ammonium salt, for example, benzyltriethylammonium chloride and benzyltri-n-butylammonium chloride are preferable. As quaternary ammonium salt-type cationic surfactant, lauryltrimethylammonium chloride and lauryldimethylamine oxide, for example, are preferable.

These inhibitors having selectivity with globulin components may be used either individually or in combination of two or more.

An amount of these inhibitors having selectivity with globulin components capable of sufficiently suppressing the reaction with globulin components during the reaction with protease may be used. When deoxycholic acid, deoxycholic acid amide, cholic acid amide, octyl glucoside, quaternary ammonium salt, or quaternary ammonium salt-type cationic surfactant is used, a concentration of about 0.01-20% is preferable, with the more preferable concentration range being 0.05-10%. A concentration may also be outside these ranges.

When concanavalin A, octyl glucoside, or betaine is used, for example, a concentration of about 0.01-10 mg/ml or 0.005-5% is applicable, with a preferable concentration range being 0.02-2 mg/ml or 0.05-10%, respectively. A concentration outside these ranges can also be used.

As the ASOx used for precisely assaying glycated proteins using the present invention, any enzyme effectively reacting with ascorbic acid contained in the sample solution can be used. ASOx originating from plants or microorganisms and the like can be given as examples. The following specific examples are given, but these should not be construed as limiting the usable enzymes in the present invention.

As examples of ASOx of plant origin, ASOx originating from cucumber (manufactured by Amano Enzyme Inc. or Toyobo Co., Ltd.) and ASOx originating from pumpkin (manufactured by Roche Co. or Toyobo Co., Ltd.) can be given.

As examples of ASOx of microorganism origin, ASOx originating from *Acremonium* (manufactured by Asahi Kasei Corporation) and ASOx originating from a microorganism (manufactured by Amano Enzyme Inc.) can be given.

The activity of ASOx was measured by the following method.

<<Method of Measuring Activity of ASOx>>

<Storing Substrate Solution>

176 mg of L ascorbic acid (manufactured by Wako Pure Chemical Industries, Ltd.) and 37 mg of EDTA (manufactured by Daiichi Pure Chemicals Co., Ltd.) are dissolved in 100 ml of 1 mM hydrochloric acid.

<Mixed Reaction Reagent>

The above storing substrate solution is diluted to 20 fold with a 90 mM dipotassium phosphate-5 mM monosodium phosphate buffer containing 0.45 mM EDTA.

<Procedure>

1 ml of the above mixed reaction reagent is placed in a small test tube and preheated at 30° C. for five minutes, then 0.10 ml of an appropriately diluted enzyme solution is added. The mixture is stirred to initiate the reaction. After the reaction for exactly 5 minutes, 3.0 ml of 0.2 N hydrochloric acid aqueous solution is added to terminate the reaction. Absorbance (As) at a wavelength of 245 nm is measured. For the blank test, 1 ml of the above reaction solution is placed in a small test tube and preheated at 30° C. for five minutes, then 3.0 ml of 0.2 N hydrochloric acid aqueous solution is added to terminate the reaction. 0.10 ml of an appropriately diluted enzyme solution is added and the mixture is stirred to measure the absorbance (Ab) at a wavelength of 245 nm. The enzyme activity is determined from the difference (Ab-As) between the absorbance (As) after the enzyme reaction and the blank test absorbance (Ab). The amount of enzyme oxidizing 1 μmol of ascorbic acid into dehydroascorbic acid in one minute at 30° C. is defined as 1 U. The calculation formula is shown below.

$$\text{Activity (U/ml)} = [(Ab-As)/10.0] \times [1/5] \times [4.10/0.10] \times [1/B]$$

10.0: Molecular absorbance coefficient (mM) of ascorbic acid at 245 nm under the conditions of pH 1.0.

5: Reaction time (min)

4.10: Total reaction solution (ml)

0.10: Amount of enzyme sample solution used for the reaction

B: Dilution magnification of the enzyme solution

The ASOx may be used in any concentration at which a sufficient amount of ascorbic acid can be eliminated during the use of a reagent when a protease and ASOx are present together, usually in the range of 0.1-100 U/ml, and preferably 1-50 U/ml, for example.

As the buffer agent having no 4-(2-hydroxyethyl)-1-piperazinyl group that can be used in combination with ASOx for precisely assaying glycated proteins according to the present invention, any buffer agent that can maintain ASOx in a stable manner when the ASOx is present together with protease can be used. Any buffer agent other than those having a 4-(2-hydroxyethyl)-1-piperazinyl group such as 3-[4-(2-hydroxyethyl)-1-piperazinyl]propane sulfonic acid (EPPS), 2-[4-(2-hydroxyethyl)-1-piperazinyl]ethane sulfonic acid (HEPES), and 2-hydroxy-3-[4-(2-hydroxyethyl)-1-piperazinyl]propane sulfonic acid (HEPPSO) can be used.

Examples of another preferable buffering agent include:
N-(2-acetamide)-2-aminoethanesulfonic acid (ACES),
N-(2-acetamide)iminodiacetic acid (ADA),
N,N-bis(2-hydroxyethyl)-2-aminoethanesulfonic acid (BES),
N,N-bis(2-hydroxyethyl)glycine (Bicine),
bis(2-hydroxyethyl)iminotris(hydroxymethyl)methane (Bis-Tris), N-cyclohexyl-3-aminopropanesulfonic acid (CAPS)
N-cyclohexyl-2-hydroxy-3-aminopropanesulfonic acid (CAPSO),
N-cyclohexyl-2-aminoethanesulfonic acid (CHES),
3-[N,N-bis(2-hydroxyethyl)amino]-2-hydroxypropanesulfonic acid (DIPSO), 2-morpholinoethanesulfonic acid (MES),
3-morpholinopropanesulfonic acid (MOPS),
2-hydroxy-3-morpholinopropanesulfonic acid (MOPSO),
piperazine-1,4-bis(2-ethanesulfonic acid) (PIPES),
piperazine-1,4-bis(2-hydroxy-3-propanesulfonic acid) (POPSO),
N-tris(hydroxymethyl)methyl-3-aminopropanesulfonic acid (TAPS),
2-hydroxy-N-tris(hydroxymethyl)methyl-3-aminopropanesulfonic acid (TAPSO),
N-tris(hydroxymethyl)methyl-2-aminopropanesulfonic acid (TES), N-[tris(hydroxymethyl)methyl]glycine (Tricine), and trishydroxymethylaminomethane (Tris).

As examples of the most preferable buffer agent, trishydroxymethylaminomethane (Tris) and piperazine-1,4-bis(2-hydroxy-3-propanesulfonic acid) (POPSO) can be given.

These buffer agents used in combination with ASOx may be used in any concentration at which the ASOx is stable in the presence of protease and the reactions of protease and ASOx are not affected, usually in the range of 1 mM to 1 M, and preferably of 5 mM to 500 mM, for example.

As the albumin protein denaturing agent and/or the compound having an S—S bond used for precisely assaying glycated proteins in the present invention, any compounds of which the reactivity of BCP to GA and NGA is equivalent can be used.

As examples of the protein denaturing agent, urea, guanidine compounds, and anionic surfactants such as sodium lauryl sulfate (SDS), polyoxyethylene alkylphenyl ether sulfate, polyoxyethylene alkyl ether sulfate, and alkyl benzene sulfonate can be given. These protein denaturing agents may be used either individually or in combination of two or more. These protein denaturing agents may be used in any concentration at which BCP equally reacts with GA and NGA, usually in the range of 0.01-10%, and preferably of 0.05-5%, for example.

As examples of the preferable compound having an S—S bond, 6,6'-dithiodinicotinic acid, 3,3'-dithiodipropionic acid, 2,2'-dithiodibenzoic acid, 4,4'-dithiodimorpholine, 2,2'-dihydroxy-6,6'-dinaphthyl disulfide (DDD), 2,2'-dithiopyridine (2-PDS), 4,4'-dithiopyridine (4-PDS), 5,5'-dithiobis-(2-nitrobenzoic acid) (DTNB), and 2,2'-dithiobis-(5-nitropyridine) can be given.

These compounds having an S—S bond may be used in any concentration at which BCP equally reacts with GA and NGA, usually in the range of 1 µM to 10 mM, and preferably of 10 µM to 5 mM, for example. A concentration outside this range is by no means excluded.

As the protease stabilizer used for precisely assaying glycated proteins according to the present invention, any compound that can suppress a decrease in the protease activity during storage of the reagent can be used. A compound that can suppress a decrease in the protease activity during storage of the reagent in a liquid state is particularly preferable.

As preferable examples of the stabilizer, dimethylsulfoxide, alcohol, water-soluble calcium salt, sodium chloride, quaternary ammonium salt, and quaternary ammonium salt-type cationic surfactant can be given. As examples of the alcohol, ethanol, propanol, ethylene glycol, and glycerol can be given. As examples of the quaternary ammonium salt and quaternary ammonium salt-type cationic surfactant, triethanolamine lauryl sulfate, lauryltrimethylammonium chloride and the like can be given.

These protease stabilizers can be used at any concentration inasmuch as a decrease in the protease activity can be suppressed during storage of the reagent, particularly at a concentration at which a decrease in the protease activity of the reagent in a liquid state can be suppressed during storage. Usually, a concentration of 0.01-30%, and preferably of 0.1-20%, is employed. Concentrations outside these ranges are not excluded.

As the stabilizer for the enzyme reacting at least with glycated amino acid used for precisely assaying glycated proteins according to the present invention, any compound that can suppress a decrease in the activity of the enzyme reacting at least with a glycated amino acid during storage of the reagent can be used. A compound that can suppress a decrease in the activity of the enzyme during storage of the reagent in a liquid state is particularly preferable.

As preferable examples of the stabilizer, sugar alcohol, sucrose, water-soluble magnesium salt, water-soluble calcium salt, ammonium sulfate, amino acid, and sarcosine can be given. As examples of the sugar alcohol, sorbitol, mannitol, trehalose, and glycerol can be given. Although any amino acids exhibit a strong stabilizing effect, preferable amino acids are proline, glutamic acid, alanine, valine, glycine, lysine, and the like.

These stabilizers for the enzyme reacting at least with a glycated amino acid can be used at any concentration inasmuch as a decrease in the activity of the enzyme reacting at least with a glycated amino acid can be suppressed during storage of the reagent. A concentration at which the decrease in the activity of the enzyme during storage of the reagent in a liquid state can be suppressed is particularly preferable. Usually, a concentration of 0.01-30%, and preferably of 0.1-20%, is employed when the stabilizer is a sugar alcohol, sucrose, amino acid, or sarcosine. When the stabilizer is water-soluble magnesium salt, water-soluble calcium salt, or ammonium sulfate, a concentration of 1 mM to 1 M, preferably of 10 mM to 500 mM, is employed. Concentrations outside these ranges are not excluded.

In preparing the composition for assaying glycated protein of the present invention, a proteolytic reagent including a protease and a glycated amino acid assay reagent to assay produced glycated amino acids or peptides are appropriately combined so that these reagents may be used in the same reaction vessel. These reagents may be supplied as a liquid product, frozen product or freeze-dried product thereof.

In preparing the proteolytic reagent used in the present invention, the pH, buffer agent, and protease concentration are determined so that proteolytic reactions are efficiently carried out. Then, the protease inhibitor having selectivity with globulin components, ASOx, and protease stabilizer are appropriately prepared and added to have the above-described effective concentrations.

When protease type-XXIV (manufactured by Sigma-Aldrich Co.) is used, for example, a reaction at pH 7-10 can be selected since this protease exhibits strong proteolytic activity at around pH 7-10. As the buffer solution, a solution of a buffer agent that does not have a 4-(2-hydroxyethyl)-1-piperazinyl group, for example, POPSO buffer solution having a buffering action in the pH range of 7.2-8.5 can be used, and a concentration of POPSO may be 1-100 mM, and preferably 10-500 mM.

The protease can be used at a concentration that can sufficiently decompose glycated proteins in a sample during the reaction time used in practice, preferably in the range of 100-500,000 PU/ml, and more preferably of 500-100,000 PU/ml.

As the combination of the protease inhibitor having selectivity with globulin components, ASOx, and protease stabilizer, a combination of 0.01-20%, and preferably 0.05-10% of 3-[(3-cholamidopropyl)dimethylammonio]propane sulfonic acid as the protease inhibitor having selectivity with globulin components, 0.1-100 U/ml, and preferably 1-50 U/ml of ascorbic acid oxidase of pumpkin origin (manufactured by Toyobo Co., Ltd.), and 0.01-30%, preferably 0.1-20% of dimethyl sulfoxide as the protease stabilizer, for example, can be used.

To formulate the reagent for assaying glycated amino acids used in the present invention, an appropriate pH is selected taking into consideration an optimum pH for the enzyme reacting at least with the glycated amino acids used to ensure an efficient reaction, the amount of enzyme to be reacted with the glycated amino acids is determined, and then a stabilizer for the enzyme reacting at least with the glycated amino acids is added.

When R-FOD or R-FOD-II (manufactured by Asahi Kasei Corporation) is used, for example, a reaction at pH 6.5-10 can be selected since these proteases can exhibit 50% or more activity of their maximum activity in the wide pH range of 6.5-10. The enzyme can be used at a concentration that can sufficiently detect the glycated amino acids in the reaction solution used, preferably in the range of 0.5-200 U/ml, and more preferably 1-50 U/ml.

Glutamic acid, for example, can be used as the stabilizer for the enzyme reacting at least with a glycated amino acid, at a concentration of 0.01-30%, and preferably of 0.1-20%.

In formulating the composition containing an enzyme reacting at least with a glycated amino acid as the first reagent and a protease as the second reagent, any conditions may be used inasmuch as the first reagent satisfies the conditions, such as a pH, salt concentration, and the like, under which the protease and the enzyme reacting at least with a glycated amino acid can exhibit activity and the second reagent satisfies the conditions under which the protease can be suitably stored.

For example, when R-FOD and protease type XXIV are used, since these enzymes have the particularly reactive pH range of 6.5-10 and 7-10 respectively, the pH range of 7-10 is selected for the first reagent, and a buffer agent with a comparatively high concentration of 20-1,000 mM, for example, is selected. On the other hand, since this protease is stable at a pH 7 or less, the pH range of 7 or less is selected for the second reagent and a buffer agent with a concentration comparatively lower than that used for the first reagent, for example, in the range of 1-50 mM, is selected. In addition, a protease stabilizer, for example, of about 1-50% dimethylsulfoxide is preferably added. In this instance, if the first reagent is used in an amount larger than the second reagent, for example at a ratio of the first reagent to the second reagent of 4:1, a stabilizer may be added to the second reagent at a higher concentration and the other conditions such as a pH deviating largely from those of the first reagent can be adopted for the second reagent.

In formulating the enzyme reaction composition for assaying glycated proteins according to the present invention, a surfactant, salt, buffer agent, pH adjusting agent, preservative, and the like, may be appropriately selected and added.

As the surfactant, for example, a polyoxyethylene alkyl ether, polyoxyethylene sorbitan fatty acid ester, polyvinyl alcohol, or the like may be added in an amount of 0.01-10%, and preferably 0.05-5%. As the salt, for example, lithium chloride, sodium chloride, potassium chloride, manganese chloride, cobalt chloride, zinc chloride, calcium chloride, or the like may be added in an amount of 1 mM to 5 M, and preferably of 10 mM to 1 M. Various buffer solutions such as Tris-HCl buffer solution, glycine-NaOH buffer solution, phosphate buffer solution, Good's buffer solution, or the like may be added in an amount of 10 mM to 2 M, and preferably of 20 mM to 1 M. Various preservatives such as sodium azide may be added appropriately in an amount of 0.01-10%, and preferably 0.05-1%.

In assaying glycated proteins using the method of the present invention, 0.001-0.5 ml of a sample is added to the composition for assaying glycated proteins of the present invention and reacted at a temperature of 37° C. When a rate assay technique is employed, changes in the amount of coenzyme, dissolved oxygen, hydrogen peroxide, or other reaction products during a period of several minutes to several tens of minutes between two specified time points after initiation of the reaction, for example, one minute between after three minutes and after four minutes from initiation of the reaction or five minutes between after three minutes and after eight minutes from initiation of the reaction, are directly or indirectly determined using the above methods. When an end point assay technique is used, changes in the amount of coenzyme, dissolved oxygen, hydrogen peroxide, or other reaction products during a certain period of time after initiation of the reaction are determined in the same manner. In this instance, the amount of glycated proteins in the sample can be determined by comparing changes in the absorbance and the like with the value determined for a sample with a known glycated protein concentration.

The reaction of the enzyme used in the present invention that can react at least with a glycated amino acid can be detected, when a dehydrogenase is used, for example, by directly assaying the change in the amount of coenzyme or indirectly assaying a reduced coenzyme that has been formed using an electron carrier such as various diaphorases or phenazine methosulfate, and a reducing-type coloring reagent such as a tetrazolium salt represented by nitrotetrazolium, WST-1 or WST-8 (manufactured by Dojindo Laboratories). Other known direct or indirect methods of assay may also be applied.

When an oxidase is used, for example, it is preferable to measure the amount of the oxygen consumption or the amount of reaction products. When R-FOD is used, for example, hydrogen peroxide and glucosone are produced as the reaction products. Both the hydrogen peroxide and glucosone can be directly or indirectly analyzed by a known method.

The amount of hydrogen peroxide can be determined, for example, by producing a coloring matter using peroxidase or the like and measuring the intensity of color, emitted light or fluorescence, by an electrochemical technique, or by producing aldehyde from alcohol using a catalase and measuring the amount of aldehyde produced.

For producing a coloring matter from hydrogen peroxide, Trinder reagent that can produce a coloring matter by oxidative condensation of a coupler such as 4-AA or 3-methyl-2-benzothiazolinone hydrazone (MBTH) and a chromogen such as phenol in the presence of peroxidase, a Leuko-type reagent that can be directly oxidized and produces a color in the presence of peroxidase, or the like can be used.

As the chromogen for a Trinder reagent, phenol derivatives, aniline derivatives, toluidine derivatives, and the like can be used. Specifically, N-ethyl-N-(2-hydroxy-3-sulfopropyl)-m-toluidine (TOOS), disodium N,N-bis(4-sulfopropyl)-3-methylaniline (TODB) (both manufactured by Dojindo Laboratories), and the like can be given.

As specific examples of the Leuko-type reagent, N-(carboxymethylaminocarbonyl)-4,4-bis(dimethylamino)-biphenylamine (DA64), 10-(carboxymethylaminocarbonyl)-3,7-bis(dimethylamino)phenothiazine (DA67) (both manufactured by Wako Pure Chemical Industries, Ltd.), and the like can be given.

A compound emitting fluorescence by oxidation such as homovanillic acid and 4-hydroxyphenylacetic acid can be used for the fluorescence method. For the chemiluminescence method, luminol, lucigenin, iso-luminol, and the like can be used as a catalyst.

When hydrogen peroxide is measured using electrodes, there are no specific limitations to the electrode used inasmuch as the electrode is made from a material allowing exchange of electrons with hydrogen peroxide. Platinum, gold, and silver can be given as examples. Conventional electrode methods such as amperometry, potentiometry, and coulometry can be used. It is possible to provide an electron carrier between the electrodes and oxidase or substrate to measure the resulting oxidation or reduction current or the amount of electricity. Any materials that can exhibit an electron transfer function can be used as the electron carrier. Ferrocene derivatives and quinone derivatives can be given as examples. It is also possible to provide an electron carrier between the electrodes and hydrogen peroxide produced by the oxidase reaction to measure the resulting oxidation or reduction current or the amount of electricity.

When the glycated protein is glycated albumin and the amount of the glycated albumin must be precisely determined, any albumin assay reagent containing a protein denaturing agent and/or a compound having an S—S bond and bromocresol purple can be used in the present invention so far as such a reagent does not produce a deviation between GA and NGA.

For example, when sodium lauryl sulfate and 5,5'-dithiobis(2-nitrobenzoic acid) are used as the protein denaturing agent and/or the compound having an S—S bond, a buffer solution with a low concentration of, for example, 1-20 mM that does not affect coloration of BPC is used, wherein sodium lauryl sulfate is used at a concentration of 0.01-10%, and preferably of 0.05-5%, and 5,5'-dithiobis(2-nitrobenzoic acid) at a concentration of 1 μM to 10 mM, and preferably of 10 μM to 5 mM. BCP is used at a pH 4.5-7.5, since BCP is manifestly colored at a pH higher than neutral.

In assaying albumin using the method of the present invention, 0.001-0.5 ml of a sample is added to the composition for assaying albumin of the present invention and reacted at a temperature of 37° C. The amount of the coloring matter at a prescribed period of time after initiation of the reaction may be determined by means of one point assay. Absorbance near 550-630 nm is measured since albumin-BCP exhibits a maximum absorbance at around 600 nm. In this instance, the amount of albumin in the sample can be determined by comparing with the absorbance determined for a sample with a known albumin concentration and the absorbance of blank (water).

Any samples containing at least a glycated protein may be used as the measuring object of the present invention. Preferable samples include blood components such as blood serum, blood plasma, blood cells, and whole blood. In addition, separated erythrocytes may be used as a preferable sample because depending on the separating conditions a separated erythrocyte sample may contain globulin components that affect the results of assay.

The glycated protein to be assayed using the composition and method for assaying glycated proteins of the present invention includes GA and GHb, but is not limited to them, and any glycated protein may be measured.

BRIEF DESCRIPTION OF THE DRAWINGS

FIG. 3 is a graph showing a measuring curve of glycated albumin obtained by the experiment in Example 6 according to the present invention.

FIG. 4 is a graph showing the effect of the types of buffer agents on stabilizing ascorbic acid oxidase in the composition for assaying glycated proteins in Example 9 according to the present invention.

FIG. 5 is a graph showing the effect of the types of stabilizers on stabilizing proteases in Example 11 according to the present invention.

FIG. 6 is a graph showing the effect of the types of stabilizers on stabilizing the enzyme capable of reacting at least with a glycated amino acid in Example 12 according to the present invention.

FIG. 9 is a graph showing the correlation between the enzymatic method and HPLC method on the result of glycated albumin measurement in Example 22 of the present invention.

FIG. 10 is a graph showing a reaction curve of the glycated protein assay reagent in Example 23 of the present invention.

BEST MODE FOR CARRYING OUT THE INVENTION

Figure 1:
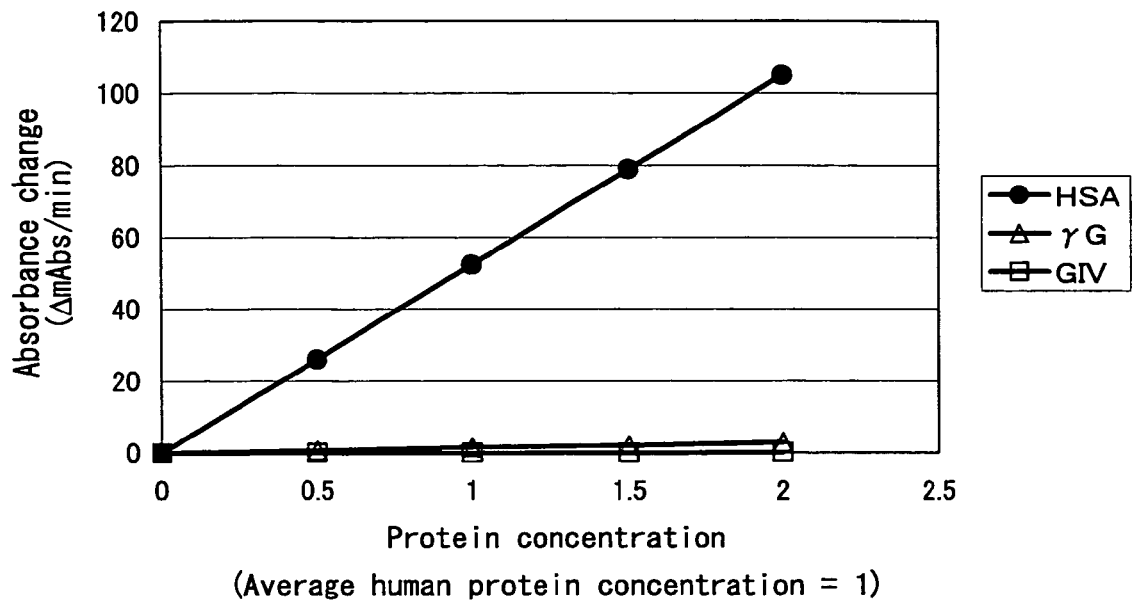
FIG. 1 is a graph showing measuring curves and reproducibility of an HSA substrate solution (4 g/dl), γ-globulin substrate solution, and globulin IV substrate solution in Example 4 according to the present invention.

The present invention will be explained by way of examples in the following description, which is not intended to limit the present invention.

EXAMPLE 1

With an objective of screening proteases that do not react with globulin components, glycated amino acids, or glycated peptides produced by reacting proteases with albumin, globulin components, and hemoglobin were assayed using R-FOD (manufactured by Asahi Kasei Corporation).

<Substrate Solutions>
1. HSA substrate solution; Albumin Human; Essentially Globulin Free; 25 mg/ml, GA %=31.9%, fructosamine (FRA) value=256 μmol/l (manufactured by Sigma-Aldrich Co.); the albumin concentration in the substrate solution was assayed using an albumin assay kit (albumin II-HA Test Wako; manufactured by Wako Pure Chemical Industries, Ltd.). GA % was assayed using a glycated albumin analyzer (GAA-2000, manufactured by ARKRAY, Inc.).
2. G-II and III substrate solutions, FRA value=48 μmol/L [Globulins Human Cohn Fraction II and III; 16.9 mg/ml (manufactured by Sigma-Aldrich Co.)]
3. G-IV substrate solution, FRA value=26 μmol/L [Globulins Human Cohn Fraction IV; 6 mg/ml (manufactured by Sigma-Aldrich Co.)]
4. G-I substrate solution, FRA value=77 μmol/L [Glovenin I: immunoglobulin preparation (manufactured by Takeda Chemical Industries, Ltd.)]
5. Hb substrate solution: Hemoglobin Human; 55 mg/ml, glycated hemoglobin rate: HbA1c=4.5% [manufactured by Sigma-Aldrich Co., the HbA1c value was determined using a glycated hemoglobin analyzer (Hi-Auto A1C HA-8150, manufactured by ARKRAY, Inc.)].

The fructosamine value of the substrate solution was measured using a fructosamine analyzer kit (Autowako Fructosamine, manufactured by Wako Pure Chemical Industries, Ltd.).

<Preparation of Protease Reaction Solution>

200 μl of a substrate solution other than Hb, 40 μl of 100 mg/ml protease solution (a solution with a concentration as close to 100 mg/ml as possible if a 100 mg/ml solution cannot be prepared, or as is if the protease solution is liquid), and 10 μl of 1 M Tris buffer solution (pH 8) were thoroughly mixed and reacted at 37° C. for 30 minutes. The reaction solution was filtered through 10,000 NMWL membrane (Ultrafree MC, manufactured by Millipore Corp.) The filtrate was served as the protease reaction sample. The same procedure was conducted using distilled water instead of the substrate to prepare a blank sample.

For the Hb substrate solution, 150 μl of the substrate solution, 60 μl of 200 mg/ml protease solution (a solution with a concentration as close to 200 mg/ml as possible if a 200 mg/ml solution cannot be prepared, or as is if the protease solution is liquid), and 5 μl of 1 M Tris buffer solution (pH 8) were thoroughly mixed and reacted at 37° C. for 60 minutes. The reaction solution was filtered through 10,000 NMWL membrane (Ultrafree MC, manufactured by Millipore Corp.). The filtrate was served as the protease reaction sample. The same procedure was conducted using distilled water instead of the substrate to prepare a blank sample.

<Assay of Glycated Amino Acids and Glycated Peptides in the Protease Reaction Sample>

<Reaction Solution Composition>

| | | |
|---|---|---|
| 50 mM | Tris buffer (pH 8.0) | |
| 0.02% | 4-AA (manufactured by Wako Pure Chemical Industries, Ltd.) | |
| 0.02% | N-ethyl-N-(2-hydroxy-3-sulfopropyl)-m-toluidine (TOOS) (manufactured by Dojindo Laboratories). | |
| 2 U/ml | R-FOD (manufactured by Asahi Kasei Corporation) | |
| 5 U/ml | POD (manufactured by Sigma-Aldrich Co.) | |

<Reaction Procedure>

300 μl of the above reaction solution for assaying glycated amino acids was added to a cell and incubated for three minutes at 37° C. Absorbance at 555 nm was measured ($A_0$). 30 μl of the protease reaction sample was then added to the cell and incubated for five minutes at 37° C. Absorbance at 555 nm was measured ($A_1$). The same procedure was conducted using the blank sample instead of the protease reaction sample. Absorbances ($A_0$ blank and $A_1$ blank) were measured. The reaction of protease with glycated proteins is indicated by the following absorbance change.

$$\Delta A = (A_1 - A_0) - (A_1 \text{ blank} - A_0 \text{ blank})$$

The reactivity (ΔA) of typical proteases with albumin, globulin, and hemoglobin at pH 8.0 is shown in Table 1.

TABLE 1

Activity of various proteases on various proteins (unit: mAbs)

| Name of protease | Origin | ΔA | | |
|---|---|---|---|---|
| | | HSA | Gl | Hb |
| Carboxypeptidase A | Cow pancreas | <1 | 50 | 13 |
| Aminopeptidase M | | <1 | 21 | <1 |
| Protease type-I | | 52 | 25 | 9 |
| Trypsin | | 11 | 15 | <1 |
| Chymotrypsin | | 25 | 103 | 7 |
| Pancreatin | | 52 | 100 | 17 |
| Carboxypeptidase W | Wheat | 7 | 18 | 1 |
| Papain | Papaya | 15 | 5 | <1 |
| Protease type-VIII | Bacillus | 90 | 84 | 33 |
| Protease type-IX | | 33 | 12 | <1 |
| Protease type-XXIV | | 172 | 91 | 2 |
| Protease type-XXVII | | 93 | 88 | 27 |
| Alcalase | | 92 | 49 | 17 |
| Orientase-22BF | | 168 | 51 | 24 |
| Orientase-90N | | 136 | 44 | 5 |
| Bioprase SP-4FG | | 63 | 37 | 9 |
| GODO-BAP | | 37 | 31 | 14 |
| Toyozyme NEP-160 | | 130 | 47 | 23 |
| Alkalophilic Protease | | 133 | 50 | 19 |
| Crystallne protease NAK | | 180 | 18 | 30 |
| Protease type XIX | Aspergillus | 20 | 22 | 33 |
| Protease type XXIII | | 49 | 27 | 11 |
| Flavourzyme | | 59 | 17 | 25 |
| Protin FN | | 37 | 20 | <1 |
| Protease A | | 44 | 16 | 19 |
| Sumiteam MP | | 76 | 35 | 27 |
| Sumizyme FP | | 37 | 7 | 11 |
| Newlase F | Rhizopus | <1 | 18 | 9 |
| PD enzyme | Penicillium | <1 | 19 | 1 |
| Pronase | Streptomyces | 109 | 152 | 42 |
| Protease type-XIV | | 112 | 125 | 41 |
| Protease type-XXI | | 75 | 35 | 11 |
| Protease type-XVII | Staphylococcus | <1 | 20 | <1 |
| Carboxypeptidase Y | Yeast | 2 | 14 | 4 |
| Proteinase K | Tritirachium | 79 | 45 | 32 |
| Aminopeptidase T | Thermus | <1 | 18 | <1 |
| Achromopeptidase | Achromobacter | 24 | 3 | 16 |
| Regelendproteinase | | 13 | 26 | 7 |

Among globulin components, only the results for the G-I substrate solution were described in Table 1, since all proteases exhibited no reaction or only a small reaction with glycated proteins in the G-IV substrate solution and the values determined for G-II and G-III substrate solutions were almost the same as that determined for the G-I substrate solution. As can be clearly seen from Table 1, proteases originated from Aspergillus and protease type XIV exhibited a good reactivity with glycated globulin in the globulin components.

However, endoproteases and exoproteases reactive with GA in albumin and GHb in hemoglobin exhibited a reaction with glycated globulin in the globulin components. These results suggest that when GA in blood serum or blood plasma, or GHb in whole blood or corpuscles are assayed, the effect of globulin components cannot be avoided only by selection of the type of protease.

EXAMPLE 2

<Screening of Globulin Component-Selective Protease Inhibitor>

Using protease type-XXIV (manufactured by Sigma-Aldrich Co.) having high reactivity with the HSA substrate solution, components that decrease the protease reaction with the above globulin substrate solutions were screened based on the HSA substrate solution.

<Reaction Solution Composition>

R-1 Proteolytic Reagent

| | |
|---|---|
| 150 mM | Tricine buffer solution (manufactured by Wako Pure Chemical Industries, Ltd.) pH 8.5 |

-continued

| | |
|---|---|
| 2,500 U/ml | Protease type-XXIV (manufactured by Sigma-Aldrich Co.) + globulin component-selective protease inhibitor (deoxycholic acid, deoxycholic acid amide, cholic acid amide, quaternary ammonium salt, or quaternary ammonium salt-type cationic surfactant: 1%, concanavalin A: 0.21 mg/ml, betaine: 0.1%, octyl glucoside: 1%, manufactured by Dojindo Laboratories) |

R-2 Glycated Amino Acid Assay Reageant

| | |
|---|---|
| 150 mM | Tricine buffer solution (Wako Pure Chemical Industries, Ltd.) pH 8.5 |
| 0.12% | 4-AA (manufactured by Wako Pure Chemical Industries, Ltd.) |
| 0.08% | TOOS (manufactured by Dojindo Laboratories) |
| 24 U/ml | R-FOD (manufactured by Asahi Kasei Corporation) |
| 20 U/ml | POD (manufactured by Sigma-Aldrich Co.) |

In the R-1 proteolytic reagent, as the deoxycholic acid amide, bisgluconamidopropyldeoxycholamide was used; as the cholic acid amide, 3-[(3-cholamidopropyl)dimethylammonio]propane sulfonic acid, 3-[(3-cholamidopropyl)dimethylammonio]-2-hydroxypropane sulfonic acid, or bisgluconamidopropylcholamide was used; as the quaternary ammonium salt, benzyltriethylan chloride or benzyltri-n-butylammonium chloride was used; and as quaternary ammonium salt-type cationic surfactant, lauryltrimethylammonium chloride or lauryldimethylamine oxide was used.

<Substrate Solutions>
1. HSA substrate solution: Albumin Human: 40 mg/ml, GA %=10.5% [manufactured by Wako Pure Chemical Industries, Ltd., the albumin concentration in the substrate solution was assayed using an albumin assay kit (albumin II-HA Test Wako; manufactured by Wako Pure Chemical Industries, Ltd.). GA % was assayed using a glycated albumin analyzer (GAA-2000, manufactured by ARKRAY, Inc.).
2. γ-globulin addition substrate solution, 17.0 mg/ml of γ-globulin [γ-Globulins Human (manufactured by Sigma-Aldrich Co.), Fructosamine value=34 μM] was added to the above HSA substrate solution.

<Reaction Procedure>
Substrate solutions (HSA substrate solution, G-I substrate solution) of 8 μl each, were added to 240 μl of R-1 incubated at 37° C. The reaction was initiated at 37° C. and exactly five minutes thereafter 80 μl of R-2 was added. Absorbances at a wavelength of 546 nm were measured before and after the addition of R-2. The difference of the two measurements was regarded as the absorbance change. The same procedure was conducted using distilled water instead of the substrate to prepare a blank sample. In addition, a reaction solution without the addition of the globulin-selective protease inhibitor was used as a control.

ΔA (HSA) was calculated by subtracting the absorbance change of the blank sample from the absorbance change obtained for the HSA substrate solution. ΔA(+γ-globulin) was calculated by subtracting the absorbance change of the blank sample from the absorbance change obtained for the substrate solution to which γ-globulin was added.

Effect of γ-globulin addition=(ΔA(+γ-globulin)−ΔA(HSA))/ΔA(HSA)×100(%)

The values obtained in the presence and absence (control) of various candidate compounds were compared. The results are shown in Table 2.

TABLE 2

Screening of globulin-selective protease inhibitors

| Name of additives | Concentration (%) | Effect of γ-globulin (%) |
|---|---|---|
| Control | | 23.8 |
| Cholic acid derivatives | | |
| Cholic acid | 1.0 | 23.0 |
| Deoxycholic acid | 1.0 | 20.0 |
| N,N-Bis(3-D-gluconamidopropyl)deoxycholamido | 1.0 | 19.9 |
| 3-[(3-cholamidopropyl)dimethylammonio]propane sulfonic acid | 1.0 | 17.9 |
| 3-[3-cholamidopropyl)dimethylammonio]-2-hydroxypropane sulfonic acid | 1.0 | 18.0 |
| N,N-Bis(3-D-gluconamidopropyl)cholamido | 1.0 | 21.0 |
| Quaternary ammonium salt | | |
| Benzyltrimethylammonium chloride | 1.0 | 23.2 |
| Benzyltriethylammonium chloride | 1.0 | 16.5 |
| Benzyltributylammonium chloride | 1.0 | 15.1 |
| Benzyltrimethylammonium bromide | 1.0 | 23.1 |
| Benzyltriethylammonium bromide | 1.0 | 22.9 |
| Quaternary ammonium salt-type cationic surfactant | | |
| Lauryltrimethylammonium chloride | 1.0 | 16.7 |
| Alkylbenzyldimethylammonium chloride | 1.0 | 23.2 |
| Lauryldimethylamine oxide | 1.0 | 17.8 |
| Others | | |
| Betaine | 0.10 | 7.6 |
| Concanavalin A | 0.21 mg/ml | 14.9 |
| Octylglucoside | 1.0 | 18.5 |

As can be seen from Table 2, the effect of inhibiting a protease reaction with globulin was identified in deoxycholic acid, deoxycholic acid amide, cholic acid amide, quaternary ammonium salt or quaternary ammonium salt-type cationic surfactant, concanavalin A, octyl glucoside, and betaine, confirming that proteins other than globulin can be mainly digested if these globulin component-selective protease inhibitors and proteases are used.

The same measurement was conducted using the Hb substrate solution instead of the HSA substrate solution, provided that when the Hb substrate solution was used, proteins were removed using trichloroacetic acid after the reaction with R-1, then the residue was neutralized and R-2 was added. In the case where the Hb substrate solution was used, deoxycholic acid, deoxycholic acid amide, cholic acid amide, quaternary ammonium salt or quaternary ammonium salt-type cationic surfactant, concanavalin A, and betaine was also confirmed to have the effect of inhibiting a protease reaction with globulin.

EXAMPLE 3

<Globulin Component-Selective Protease Inhibitive Effect of 3-[(3-cholamidopropyl)dimethylammonio]propane sulfonic acid>

Globulin Component-selective Protease Inhibitive Effect of 3-[(3-cholamidopropyl)dimethylammonio]propane sulfonic acid was confirmed using various proteases.

R-1 Proteolytic Reagent

| 150 mM | Tricine buffer solution (Wako Pure Chemical Industries, Ltd.) pH 8.5 |
| 2,500 U/ml | Protease* |
| 1% | 3-[(3-cholamidopropyl)dimethylammonio]propane sulfonic acid |

*Orientase 22BF (manufactured by HBI Enzymes, Inc.), Protease type-VIII, Protease type-XIV, and Pprotease type-XXVII (above, manufactured by Sigma-Aldrich Co.) were used as the protease.

R-2 Glycated Amino Acid Assay Reagent
The same as in Example 2.

<Substrate Solutions>
The same as in Example 2.

<Reaction Procedure>
The effects of γ-globulin addition in the presence and absence (control) of sulfuric acid-3-[(cholamidopropyl) dimethylammonio]-1-propane were compared in the same manner as in Example 2. The results are shown in Table 3. In the column of judgment, the cases in which the effect of adding γ-globulin was significantly decreased was indicated by ○.

TABLE 3

Globulin component-selective protease inhibitive effect of [(3-cholamidopropyl)dimethylammonio]propane sulfonic acid

| Name of protease | Concentration (%) | Effect of γ-globulin (%) | Judgment |
|---|---|---|---|
| Orientase-22BF | 0.0 | 20.8 | — |
|  | 1.0 | 11.8 | ○ |
| Protease type-VIII | 0.0 | 20.3 | — |
|  | 1.0 | 15.6 | ○ |

TABLE 3-continued

Globulin component-selective protease inhibitive effect of [(3-cholamidopropyl)dimethylammonio]propane sulfonic acid

| Name of protease | Concentration (%) | Effect of γ-globulin (%) | Judgment |
|---|---|---|---|
| Protease type-XIV | 0.0 | 30.6 | — |
|  | 1.0 | 20.6 | ○ |
| Protease type-XXVII | 0.0 | 28.6 | — |
|  | 1.0 | 19.0 | ○ |

As can be seen from Table 3, Orientase 22BF, Protease type-VIJI, Protease type-XIV, and Protease type-XXVII decreased the protease reaction with the γ-globulin substrate in the presence of 3-[(3-cholamidopropyl)dimethylammoniolpropane]sulfonic acid, whereas all of these proteases maintained the reaction with the HSA substrate. These results have made it clear that the globulin component-selective protease inhibitors of the present invention are effective irrespective of types of proteases.

In addition, even when GHb is assayed, the effect of the globulin components could also be avoided using the present invention.

EXAMPLE 4

<Dilution Linearity of Glycated Albumin>

| 150 mM | Tricine buffer solution (Wako Pure Chemical Industries, Ltd.) pH 8.5 |
| 2,500 U/ml | Protease type-XXVII (manufactured by Sigma-Aldrich Co.) |
| 1% | Sulfuric acid-3-[(cholamidopropyl)-dimethylammonio]-2-hydroxy-1-3-[(3-cholamidopropyl)dimethylammonio]-2-hydroxypropane sulfonic acid (manufactured by Sigma-Aldrich Co.) |

R-2 Glycated Amino Acid Assay Reagent
The same as in Example 2.

<Substrate Solutions>
1. HSA substrate solution: the same as in Example 1, provided that the solution at a concentration of 4.0 g/dl was used.
2. γ-globulin substrate solution: the same as in Example 2
3. Globulin IV substrate solution: the same as in Example 1

<Procedure>
The HSA substrate solution (4 g/dl), γ-globulin (γG) substrate solution (1.7 g/dl), and globulin IV (GIV) substrate solution (1.7 g/dl) were diluted to a magnification of 0.0, 0.5, 1.0, 1.5, and 2.0-fold to confirm the dilution linearity. The same procedure as in Example 3 was followed, provided that the 1.0-fold dilution sample of HAS was assayed 10 times to calculate the CV value. The results are shown in FIG. 1.

As can be seen from FIG. 1, the absorbance did not change by changing the concentration of γ-globulin substrate solution or globulin IV (GIV) substrate solution. On the other hand, the HSA substrate solution exhibited a good linearity corresponding to the concentration, indicating that glycated albumin can be assayed without being substantially affected by globulin components. Excellent reproducibility of CV value=0.9% has been confirmed with the HSA 1.0-fold concentration indicating that, if the method of assaying of the present invention is used, glycated albumin can be selectively assayed with good sensitivity and excellent reproducibility in a reaction time of 10 minutes.

EXAMPLE 5

<Dilution Linearity of Glycated Hemoglobin>

| 77 mM | Tris buffer solution (pH 8.0) |
|---|---|
| 2,500 U/ml | Protease type XIV (manufactured by Sigma-Aldrich Co.) |
| 1% | 3-[(3-cholamidopropyl)dimethylammonio]-2-hydroxypropane sulfonic acid (manufactured by Sigma-Aldrich Co.) |

R-2 Glycated Amino Acid Assay Reagent
The same as in Example 2.

<Substrate Solutions>
The same Hb substrate solution as in Example 1 and the same γ-globulin substrate solution and globulin IV substrate solution as in Example 4 were used.

<Procedure>
Samples with 0.0, 0.5, 1.0, 1.5, and 2.0-fold concentrations of the Hb substrate solution (4 g/dl), γ-globulin substrate solution (1.7 g/dl), and globulin IV substrate solution (1.7 g/dl) were prepared to confirm the dilution linearity. The same procedure as in Example 1 was followed, provided that the 1.0-fold dilution sample of Hb was assayed 10 times to calculate the CV value. The results are shown in FIG. 2.

Figure 2:
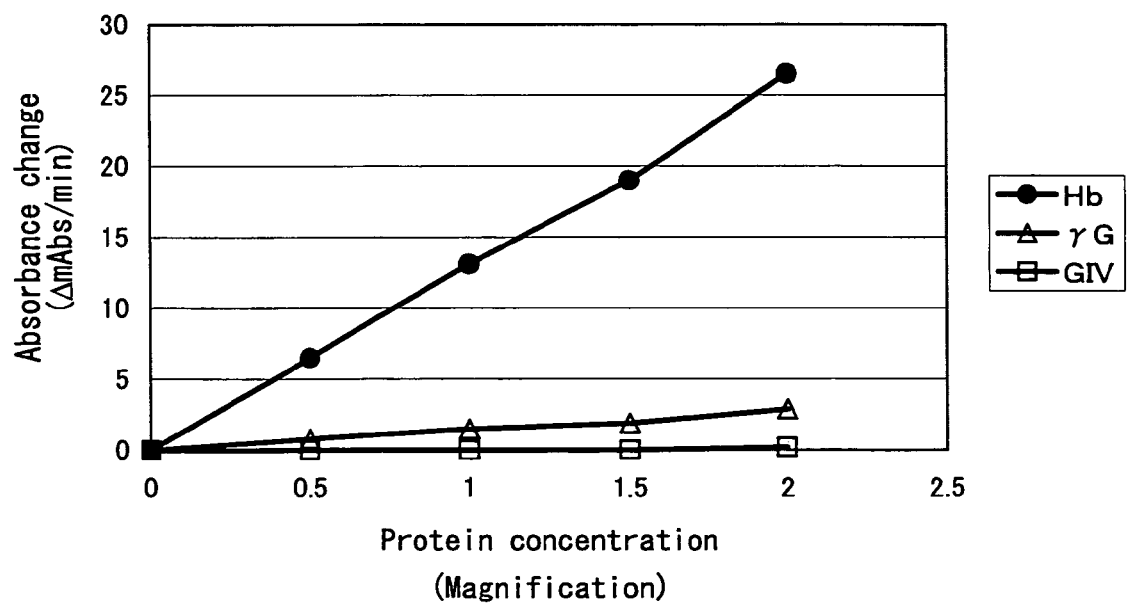
FIG. 2 is a graph showing measuring curves and reproducibility of an Hb substrate solution (4 g/dl), γ-globulin substrate solution, and globulin IV substrate solution in Example 5 according to the present invention.

As can be seen from FIG. 2, the absorbance did not change by changing the concentration of γ-globulin substrate solution and globulin IV (GIV) substrate solution. On the other hand, the Hb substrate solution exhibited a good linearity corresponding to the concentration, indicating that glycated hemoglobin can be assayed without being substantially affected by globulin components. Excellent reproducibility of CV value=2.0% has been confirmed with the Hb 1.0-fold concentration indicating that if the method of assaying of the present invention is used, glycated hemoglobin can be selectively assayed with good sensitivity and excellent reproducibility in a reaction time of 10 minutes.

EXAMPLE 6

<Linearity of Glycated Albumin>

R-1 Proteolytic Reagent
The same as in Example 4.

R-2 Glycated Amino Acid Assay Reagent
The same as in Example 4.

<Substrate solutions>
Blood serum A)* blood serum OF diabetic GA %=32.9%; albumin concentration: 4.3 g/dl
Blood serum b)* blood serum of a healthy person GA %=16.4%; albumin concentration: 4.1 g/dl
  *The above blood serums A) and B) was mixed at ratios 10:0, 8:2, 6:4, 4:6, 2:8, and 0:10 to produce mixed samples.

<Procedure>
The same as in Example 3.
The results are shown in FIG. 3.

As can be seen from FIG. 3, excellent linearity was obtained using samples with the same albumin concentration and a different glycated albumin ratio. Accordingly, the method for assaying glycated proteins of the present invention was confirmed to quantitatively analyze glycated albumin in blood serum and blood plasma in practice. In addition, since the same linearity was demonstrated by using a hemoglobin substrate solution prepared by hemolyzing erythrocytes instead of blood serum, the method for assaying glycated proteins of the present invention was confirmed to quantitatively analyze glycated emoglobin as well.

EXAMPLE 7

<Correlation Between Glycated Albumin HPLC and Enzymatic Method (the Present Invention)>

R-1 Proteolytic Reagent
The same as in Example 4.

R-2 Glycated Amino Acid Assay Reagent
The same as in Example 4.

| Blood serum of diabetics | 14 samples |
|---|---|
| Blood serum of healthy persons | 25 samples |

<Procedure>
The same procedure as in Example 2 was followed.

A correlation between the enzymatic method of the present invention and a known HPLC method was identified using 14 blood serum samples of diabetics. The glycated albumin ratio was measured by the HPLC method using a glycated albumin analyzer (GAA-2000, manufactured by ARKRAY, Inc.). The absorbance change obtained by the method of the present invention exhibited a remarkably high correlation with the glycated albumin ratio (coefficient of correlation r=0.991), confirming that the assay method of the present invention can precisely measure glycated albumin.

EXAMPLE 8

<Effect of Buffer Agent Types on Stabilization of Ascorbic Acid Oxidases>

<Reaction solution composition>

| 150 mM | Various buffer solutions (pH 8.0) |
|---|---|
| 2,500 U/ml | Protease type-XXIV (manufactured by Sigma-Aldrich Co.) or Pronase (manufactured by Sigma-Aldrich Co.) |
| 10 U/ml | Ascorbic acid oxidase (ASO-311, manufactured by Toyobo Co., Ltd.) or heat-stable type ascorbic acid oxidase (ASO-312, manufactured by Toyobo Co., Ltd.) |

R-1 As the buffer agent in the proteolytic reagent, 3-[4-(2-hydroxyethyl)-1-piperazinyl]propanesulfonic acid (EPPS), 2-[4-(2-hydroxyethyl)-1-piperazinyl]ethanesulfonic acid (HEPES), 2-hydroxy-3-[4-(2-hydroxyethyl)-1-piperazinyl]Propanesulfonic acid (HEPPSO), trishydroxymethylaminomethane (Tris), piperazine-1,4-bis(2-hydroxy-3-propanesulfonic acid) (POPSO) (above compounds: manufactured by manufactured by Dojindo Laboratories) and phosphoric acid (Wako Pure Chemical Industries, Ltd.) were used.

<Procedure>

The above reaction solutions were prepared using various buffer agents. A portion of each solution was used as a control after measuring the ascorbic acid oxidase activity. The above-described <<Method for Measuring the Activity of Ascorbic Acid Oxidase (ASOx)>> was employed for the activity measurement. The remaining portion of reaction solutions was stored for two days at room temperature, and the activity was measured in the same manner. The ratio of the activity after storage for two days at room temperature to the activity of the control was calculated to compare the stability of ascorbic acid oxidases. The results are shown in Table 4.

TABLE 4

Effect of buffer agent types on stabilization of ascorbic acid oxidases

| | Relative activity (%) | | | |
|---|---|---|---|---|
| | Protease type XXIV | | Pronase | |
| Buffer agent | ASO-311 | ASO-312 | ASO-311 | ASO-312 |
| EPPS | 35 | 30 | 13 | 31 |
| HEPES | 31 | 34 | 17 | 37 |
| HEPPSO | 37 | 22 | 14 | 34 |
| Tris | 52 | 44 | 55 | 62 |
| POPSO | 62 | 56 | 80 | 80 |
| Phosphoric acid | 77 | 86 | 88 | 108 |

As can be seen from Table 4, ascorbic acid oxidases were clearly more stable in the presence of a protease the case where trishydroxymethylaminomethane (Tris), piperazine-1,4-bis(2-hydroxy-3-propanesulfonic acid) (POPSO) or phosphoric acid that does not have a 4-(2-hydroxyethyl)-1-piperazinyl group was used as the buffer agent rather than the case where 3-[4-(2-hydroxyethyl)-1-piperazinyl]propanesulfonic acid (EPPS), 2-[4-(2-hydroxyethyl)-1-piperazinyl]-ethanesulfonic acid (HEPES), or 2-hydroxy-3-[4-(2-hydroxyethyl)-1-piperazinyl]propanesulfonic acid (HEPPSO) having a 4-(2-hydroxyethyl)-1-piperazinyl group was used as the buffer agent.

It was also clear that the same effects were confirmed irrespective of the types of ascorbic acid oxidases and proteases.

EXAMPLE 9

<Effect of Buffer Agent Types on Stabilization of Ascorbic Acid Oxidases in Compositions for Assaying Glycated Proteins>

<Reaction Solution Composition>

R-1 Proteolytic Reagent

| R-1 Proteolytic reagent | |
|---|---|
| 150 mM | Various buffer solutions (pH 8.0) |
| 2,500 U/ml | Protease type-XXIV (manufactured by Sigma-Aldrich Co.) |
| 2.0 mM | 4-Aminoantipyrine (manufactured by Wako Pure Chemical Industries, Ltd.) |
| 10 U/ml | Ascorbic acid oxidase (manufactured by Toyobo Co., Ltd.) |

R-2 Glycated Amino Acid Assay Reagent

| 150 mM | HEPES buffer solution (manufactured by Wako Pure Chemical Industries, Ltd.) pH 7.5 |
|---|---|
| 6.0 mM | TOOS (manufactured by Dojindo Laboratories) |
| 24 U/ml | R-FOD (manufactured by Asahi Kasei Corporation) |
| 20 U/ml | POD (manufactured by Sigma-Aldrich Co.) |

EPPS, HEPES, HEPPSO, Tris, and POPSO were used as buffer agents in the R-1 proteolytic reagent.

<Control Substrate Solution and Ascorbic Acid-Addition Substrate Solution>

An ascorbic acid-addition substrate solution was prepared by adding one volume of ascorbic acid (1 g/dl) (manufactured by Kokusan Chemical Co., Ltd.) to nine volume of human pool blood serum. A solution prepared by adding distilled water instead of ascorbic acid was used as a control substrate solution.

<Reaction Procedure>

8 μl of the control substrate solution or ascorbic acid-addition substrate solution was added to 240 μl of R-1 incubated at 37° C. The reaction was initiated at 37° C. and exactly 5 minutes thereafter 80 μl of R-2 was added. Absorbance at 555 nm was measured before the addition of R-2 and five minutes after the addition of R-2. $\Delta A_0$ was calculated by subtracting the absorbance change obtained from a blank sample using distilled water instead of the substrate solution from the absorbance change obtained from the absorbance measurement on the control substrate solution and ascorbic acid-addition substrate solution. The same reaction solution R-1 was stored at room temperature for 24 hours, and the absorbance was measured in the same manner to calculate $\Delta A_{24}$. The ratio of $\Delta A_0$ and $\Delta A_{24}$ obtained from the ascorbic acid-addition substrate solution was calculated assuming the absorbance change obtained from the control substrate solution as 100. The results are shown in FIG. 4.

Since ascorbic acid exhibits significantly negative effects on the measurement system, glycated protein signals cannot be observed if the elimination reaction is omitted when the concentration of 100 mg/dl is used. As can be seen from FIG. 4, the glycated protein assaying systems using Tris or POPSO that does not have a 4-(2-hydroxyethyl)-1-piperazinyl group exhibited no change in the ascorbic acid eliminating capability after storing for 24 hours at room temperature. On the other hand, the systems using EPPS, HEPES, or HEPPSO having a 4-(2-hydroxyethyl)-1-piperazinyl group as the buffering agent exhibited almost no ascorbic acid eliminating capability after storing for 24 hours at room temperature. Based on the above results, ascorbic acid oxidases were found to be more stable in the assay system using a buffer agent not having a 4-(2-hydroxyethyl)-1-piperazinyl group than in the system using a buffer agent having the 4-(2-hydroxyethyl)-1-piperazinyl group in a glycated protein assay reagent in which both a protease and ascorbic acid oxidase are present.

In addition, the above results clearly demonstrate that the present invention is useful for assaying glycated albumin, fructosamine, and glycated hemoglobin.

EXAMPLE 10

<Difference in the Reactivity of Bromocresol Purple to Glycated Albumin and Non-Glycated Albumin, and the Effect of Protein Denaturing Agent and/or Compound Having S—S Bond>

<Reaction Solution Reageant>

| 10 mM | Tris-HCl buffer solution (pH 8.0) + protein denaturing agent and/or compound having S—S bond at various concentrations; distilled water was added as a control |
|---|---|

R-2 Albumin Coloring Reagent

| 200 mM | Succinic acid buffer solution (manufactured by Wako Pure Chemical Industries, Ltd.) pH 5.5 |
|---|---|
| 0.15 mM | Bromocresol purple (manufactured by Wako Pure Chemical Industries, Ltd.) |
| 0.3% | Tx-100 (manufactured by Wako Pure Chemical Industries, Ltd.) |

The following compounds 1)-9) were used as the protein denaturing agent and/or the compound having S—S bond in the R-1 pretreatment reagent.

1) 6,6'-dithiodinicotinic acid: 100 mM
2) 3,3'-dithiodipropionic acid: 100 mM
3) 2,2'-dithiodibenzoic acid: 100 mM
4) 4,4'-dithiodimorpholine: 100 mM
5) DTNB (50 mM)
6) DDD (33 mM)
7) 2-PDS (25 mM)
8) 4-PDS (50 mM)
9) SDS (0.3%)

1)-5) manufactured by Wako Pure Chemical Industries, Ltd.
6)-9) manufactured by Dojindo Laboratories <Samples>

Glycated lbumin, non-glycated albumin, blood serum of healthy persons, and blood serum of patients were used as samples, and distilled water was used as a blank. Glycated albumin and non-glycated albumin were obtained from human blood serum, albumin was purified by known method and using a boric acid-immobilized resin.

<Reaction Procedure>

2 µl of a sample was added to 160 µl of the pretreatment reagent incubated at 37° C. The reaction was initiated at 37° C. and exactly five minutes thereafter 160 µl of the albumin coloring reagent was added. Absorbance at 600 nm was measured before the addition of the albumin coloring reagent and five minutes after the addition of the albumin coloring reagent. A calibration curve was prepared using distilled water and a sample with a known albumin concentration instead of the sample. A sample was separately assayed by an immune method using a latex reagent (LX reagent, Alb-II, manufactured by Eiken Chemical Co., Ltd.) as a control. The results are shown in Table 5.

TABLE 5

| Reagent | Immunological method | BCP method | | | | | | | | | |
|---|---|---|---|---|---|---|---|---|---|---|---|
| | | None | 1 | 2 | 3 | 4 | 5 | 6 | 7 | 8 | 9 |
| Water | 0.1 | 0.0 | 0.1 | 0.0 | 0.0 | 0.0 | 0.1 | 0.0 | 0.1 | 0.0 | 0.0 |
| NGA | 37.5 | 36.1 | 35.6 | 35.7 | 38.0 | 39.5 | 38.4 | 36.9 | 36.8 | 36.2 | 37.4 |
| GA | 8.1 | 7.9 | 7.6 | 7.9 | 7.7 | 7.7 | 8.7 | 7.6 | 7.8 | 7.5 | 7.8 |
| Blood serum of healthy parsons | 43.0 | 38.4 | 38.2 | 37.9 | 40.1 | 41.3 | 38.3 | 39.1 | 38.9 | 38.8 | 43.7 |
| Blood serum of patients | 40.5 | 36.2 | 36.7 | 37.0 | 35.0 | 31.3 | 35.5 | 37.7 | 36.8 | 36.2 | 40.7 |

As can be seen from Table 5, the value for NGA was unexpectedly low in the BCP method without a pretreatment. In the same manner, the deviation of the immune method from the BCP method was smaller in the patients with a small amount of NGA than in the healthy persons with a large amount of NGA. The deviation from the immune method significantly decreased by pretreatment with the protein denaturing agent and/or the compound having S—S bond. Among them, the effect of 2,2'-dithiosalicylic acid and 4,4'-dithiodimorpholine, DDD, 2-PDS, 4-PDS, DTNB, and sodium laurylsulfate was particularly remarkable. As a result, it has been confirmed that if a sample is pretreated with a protein denaturing agent and/or a compound having S—S bond and BCP is reacted simultaneously with or following the pretreatment when assaying the ratio of glycated albumin, an error to the negative side can be avoided due to NGA, ensuring precise determination of the ratio of glycated albumin.

EXAMPLE 11

<Stabilization of Protease>

<Reaction Solution Composition>

R-1 Proteolytic Reagent

| 150 mM | Tris-HCl buffer solution (pH 8.5) |
|---|---|
| 5,000 PU/ml | Protease type-XXIV (manufactured by Sigma-Aldrich Co.) |
| 8 mM | 4-Aminoantipyrine (manufactured by Dojindo Laboratories) |
| 15 U/ml | Peroxidase |

-continued

| | |
|---|---|
| 1.0% | 3-[(3-cholamidopropyl)dimethylammonio]-2-hydroxypropane sulfonic acid (manufactured by Sigma-Aldrich Co.) + Protease stabilizer with various concentrations (distilled water was added as a control.) |

R-2 Glycated Amino Acid Assay Reagent

| | | |
|---|---|---|
| 150 mM | Tris-HCl buffer solution (pH 8.5) | |
| 24 U/ml | R-FOD-II (manufactured by Asahi Kasei Corporation) | |
| 12 mM | TOOS (manufactured by Dojindo Laboratories) | |

The following compounds 1)-7) were used as the protease stabilizer in the pretreatment reagent.

| | | |
|---|---|---|
| 1) | 0.5 mM | Magnesium chloride |
| 2) | 10 mM | Calcium chloride |
| 3) | 100 mM | Sodium chloride |
| 4) | 0.1% | Ethylene glycol (EtGly) |
| 5) | 10% | Dimethylsulfoxide (DMSO) |
| 6) | 1% | Ethanol (EtOH) |
| 7) | 0.1% | Triethanolamine lauryl sulfate (TEALS) |

1)-7) manufactured by Wako Pure Chemical Industries, Ltd.

<Sample>

5 g/dl HSA (LOT38H7601; manufactured by Sigma-Aldrich Co.)

<Reaction Procedure>

8 μl of a sample was added to 240 μl of the proteolytic reagent incubated at 37° C. The reaction was initiated at 37° C. and exactly 5 minutes thereafter 80 μl of the glycated amino acid assay reagent was added. Absorbance at 546 nm was measured before the addition of the glycated amino acid assay reagent and five minutes after the addition of the glycated amino acid assay reagent. $\Delta A_0$ was calculated by subtracting the absorbance change obtained from a blank sample using distilled water instead of the substrate solution from the absorbance change obtained from the absorbance measurement on the substrate solution. The same reaction solution proteolytic reagent was stored at 37° C. for 24 hours, and the absorbance was measured in the same manner. $\Delta A_{24}$ was calculated based on the results of the absorbance measurement. A relative sensitivity for the experiment using the reagent containing a stabilizer to the experiment using the reagent not containing a stabilizer was calculated assuming that $\Delta A_0$ obtained using the reagent not containing a stabilizer and used without storing is 100%. The results are shown in FIG. 5.

As can be seen from FIG. 5, the relative sensitivity decreased to 60% when a stabilizer was not used, indicating the stabilization effect of the proteolytic reagent. In the experiment in which a stabilizer was added, the stabilization effect by the addition of calcium chloride, sodium chloride, DMSO, EtOH, or TEALS was observed. Of these, calcium chloride and DMSO exhibited almost no decrease in performance. The stability experiment using DMSO and calcium chloride was continued to find that almost no decrease in performance was seen during storage for 4 weeks at 37° C. In addition, these compounds were confirmed to have a storage stability effect of one year or more when stored in a liquid state in a refrigerator.

EXAMPLE 12

<Stabilization of Enzyme Reacting at Least with Glycated Amino Acid>

<Reaction Solution Composition>

R-1 Proteolytic Reagent

| | | |
|---|---|---|
| 150 mM | Tris-HCl buffer solution (pH 8.5) | |
| 8 mM | 4-Aminoantipyrine (manufactured by Dojindo Laboratories) | |
| 15 U/ml | Peroxidase | |

R-2 Glycated Amino Acid Assay Reagent

| | | |
|---|---|---|
| 150 mM | Tris-HCl buffer solution (pH 8.5) | |
| 24 U/ml | R-FOD-II (manufactured by Asahi Kasei Corporation) | |
| 12 mM | TODB (manufactured by Dojindo Laboratories) + Protease stabilizer with various concentrations (distilled water was added as a control.) | |

The following compounds 1)-15) were used as the stabilizer for enzymes reacting at least with glycated amino acid in the glycated amino acid assay reagent.

| | | |
|---|---|---|
| 1) | 5% | Mannitol |
| 2) | 5% | Sorbitol |
| 3) | 5% | Sucrose |
| 4) | 5% | Trehalose |
| 5) | 0.5 mM | Calcium chloride |
| 6) | 0.5 mM | Magnesium chloride |
| 7) | 3% | L-Glutamic acid (Glu) |
| 8) | 3% | L-Glutamine (Gln) |
| 9) | 3% | L-Proline (Pro) |
| 10) | 3% | L-Alanine (Ala) |
| 11) | 3% | L-Valine (Val) |
| 12) | 3% | Glycine (Gly) |
| 13) | 3% | L-Lysine (Lys) |
| 14) | 3% | Sarcosine |
| 15) | 100 mM | Ammonium sulfate |

1)-14) manufactured by Wako Pure Chemical Industries, Ltd.

<Sample>

0.5 mM FZL.

<Reaction Procedure>

8 μl of a sample was added to 240 μl of the proteolytic reagent incubated at 37° C. The reaction was initiated at 37° C. and exactly five minutes thereafter 80 μl of the glycated amino acid assay reagent was added. Absorbance at 546 nm was measured before the addition of the glycated amino acid assay reagent and five minutes after the addition of the glycated amino acid assay reagent. ☐A0 was calculated by subtracting the absorbance change obtained from a blank sample using distilled water instead of the substrate solution from the absorbance change obtained from the absorbance measurement on the substrate solution. The same reaction solution glycated amino acids assay reagent was stored at 37° C. for two days, and the absorbance was measured in the same manner. $\Delta A_{24}$ was calculated based on the results of the absorbance measurement. A relative sensitivity for the experiment using the reagent containing a stabilizer to the experiment using the reagent not containing a stabilizer was calculated assuming that $\Delta A_0$ obtained using the reagent not containing a stabilizer and used without storing is 100%. The results are shown in FIG. 6.

As can be seen from FIG. 6, the relative sensitivity decreased to 30% when a stabilizer was not used, indicating the stabilization effect of the glycated amino acid assay reagent. In the experiment in which a stabilizer was added, the stabilization effect by the addition of mannitol, sorbitol, sucrose, trehalose, calcium chloride, magnesium chloride, L-glutamic acid, L-glutamine, L-proline, L-alanine, L-valine, glycine, L-lysine, sarcosine, and ammonium sulfate was observed. Of these, sugar alcohol, amino acid, and sarcosine exhibited a particularly strong stabilization effect. The stability experiment using L-alanine, glycine, or sarcosine was continued to find that almost no decrease in performance was seen during storage for four weeks at 37° C. In addition, these compounds were confirmed to have a storage stability effect of one or more years when stored in a liquid state in a refrigerator.

EXAMPLE 13

<Preparation of Mutated FOD Gene-Containing DNA Fragment Library>

Synthesis of an oligonucleotide having the base sequence of 1-30 in the base sequence of the sequence table Sequence ID No. 5 and an oligonucleotide having the base sequence of 1-30 in the base sequence of the sequence table Sequence ID No. 5 were consigned to BEX Co., Ltd. Using a Taq polymerase kit (manufactured by Takara Shuzo Co., Ltd.), a PCR was conducted using DNA encoding FOD protein originating from *Fusarium oxysporm* IFO-9972 as a template according to the manual attached to the kit, thereby amplifying the FOD structural gene. The reaction was conducted with the addition of $Mg^{++}$ ion equivalent to the final concentration of 0.5 mM to the reaction solution and at unevenly distributed base concentrations of dATP: 0.51 mM, dCTP: 0.20 mM, dGTP: 1.15 mM, and dTTP: 3.76 mM to promote the mutagenesis efficiency.

EXAMPLE 14

<Preparation of Mutant FOD Recombinant Library>

DNA fragments containing amplified FOD gene obtained in Example 13 was digested with restriction endonucleases NcoI and EcoRI, incorporated into plasmid oTV119N (manufactured by Takara Shuzo Co., Ltd.) treated with the same restriction endonucleases, and introduced into *Escherichia coli* JM109 strain (manufactured by Toyobo Co., Ltd.). Cells were cultured overnight at 37° C. in a LB agar plate culture medium (manufactured by DIFCO Co.) containing 100 µg/ml of ampicillin to form colonies of a transformant.

EXAMPLE 15

<Screening of Lysine-Specific Mutated FOD>

The colonies of the library prepared in Example 14 were replicated in two sheets of LB agar plate culture media, each containing 100 µg/ml of ampicillin and 1 mM IPTG (manufactured by Wako Pure Chemical Industries, Ltd.). An LB agar (0.3%) culture medium containing 5 U/ml of peroxidase (manufactured by Asahi Kasei Corporation), 0.02% of orthodianisidine (manufactured by Wako Pure Chemical Industries, Ltd.), 2.0 mM of glycated valine or glycated lysine (prepared by the method of Hashiba et al. Hashiba, H. (1976) J. Agric. Food Chem., 24, 70) was layered over each medium. After incubation at 37° C. for eight hours, oxygen radicals formed by the oxidation of glycated amino acid with FOD and coloration of colonies produced by dianisidine were observed. Colonies dyed with glycated lysine into dark purple and not dyed with glycated valine were screened in this manner, and 164 strains of the corresponding colonies were obtained.

EXAMPLE 16

<Preparation of Cell Extract Fluid of Mutated FOD Candidate Strains>

164 strains of mutant colonies obtained in Example 15 were cultured for 16 hours at 30° C. in 1.5 ml of a 3.7% BHI liquid medium (manufactured by DIFCO Co.) containing 50 µg/ml of ampicillin and 1 mM of IPTG. 1 ml of the culture broth was centrifuged (15,000 G for one minute at 4° C.) to collect cells. 200 µl of 10 mM Tris-HCl buffer solution (pH 8.0) was added to the collected cells. After crushing the cells using an ultrasonic breaker, the mixture was centrifuged (14,000 G for five minutes at 4° C.) to obtain a cell extract as a supernatant.

EXAMPLE 17

<Substrate Specificity Verification of Mutant FOD>

The glycated amino acid substrate specificity of FOD-mutated recombinant contained in the cell extract prepared in Example 16 was measured using the above-mentioned FOD enzyme activity measuring method. As a result, two mutants of which the reactivity with glycated valine is less than $\frac{1}{1,000}$ the reactivity with glycated lysine were identified among candidate strains. These were regarded as the target mutants.

EXAMPLE 18

<Extraction of Recombinant Plasmid>

The mutants selected in Example 17 were inoculated in 1.5 ml of LB liquid medium containing 50 µg/ml of ampicillin and cultured with shaking at 37° C. for 16 hours. Plasmids were extracted according to a conventional method. These plasmids were named pcmFOD1 and pcmFOD2.

EXAMPLE 19

<Determination of Base Sequence of Mutant FOD Genes>

The base sequences of the mutant FOD genes obtained in Example 18 were determined according to the dideoxy method. As a result, the two mutants were found to possess the same structure, with the 1115th A in the base sequence of the sequence table Sequence ID No. 1 being replaced with G and the 372nd lysine in the amino acid sequence of the encoded recombinant mutant FOD in the sequence table Sequence ID No. 1 being replaced with arginine.

EXAMPLE 20

<Confirmation of Substrate Specificity of Each Mutant>

To observe the effect of replacement with other amino acids at the mutated amino acid site identified in Example 19, the site-directed mutagenesis according to the method of Kunkel et al. was carried out. Synthesis of an oligonucleotide having the base sequence of 1-27 in the sequence table Sequence ID No. 7 was consigned to an outside source (BEX Co., Ltd.). The oligonucleotide was subjected to the site-directed mutagenesis using the Mutan-K kit (manufactured by Takara Shuzo Co., Ltd.) according to the manual attached to the kit. The mutant gene obtained was incorporated again into the expression plasmid pTV119N, introduced into *Escherichia coli* host, and cultured at 30° C. for 16 hours in a 3.7% BHI liquid medium containing 50 μg/ml of ampicillin and 1 mM of IPTG to produce mutant FOD protein. The substrate specificity was measured in the same manner as in Examples 16 and 17 using a plurality of mutants produced by the above experiment to find that mutants replaced with tryptophan, methionine, threonine, valine, alanine, serine, cysteine, or glycine other than arginine exhibit the same glycated lysine-specific substrate specificity as the mutant replaced with arginine. The results are shown in Table 6.

TABLE 6

| Reactive 327th amino acid | Kcat Substrate glycated amino acid Lysine (a) | Kcat Substrate glycated amino acid Valine (b) | Kcat Reactivity ratio (a)/(b) | Km/Ko Substrate glycated amino acid Lysine (a) | Km/Ko Substrate glycated amino acid Valine (b) | Km/Ko Reactivity ratio (a)/(b) |
|---|---|---|---|---|---|---|
| Lysine (wild type) | 14900 | 549 | 27.1 | 5650 | 596 | 9.5 |
| Arginine | 351 | 0.45 | 788 | 447 | 1.00 | 440 |
| Tryptophan | 248 | below limit | — | 319 | 0.11 | 2980 |
| Methionine | 853 | 1.14 | 745 | 638 | 0.46 | 1480 |
| Valine | 1470 | 1.04 | 1420 | 1940 | 1.01 | 1930 |
| Threonine | 952 | 0.47 | 2010 | 866 | 0.93 | 927 |
| Alanine | 1790 | 1.21 | 1480 | N.D. | N.D. | N.D. |
| Serine | 1250 | 1.68 | 747 | N.D. | N.D. | N.D. |
| Cysteine | 569 | 0.37 | 1560 | N.D. | N.D. | N.D. |
| Glycine | 271 | 0.74 | 365 | N.D. | N.D. | N.D. |

Figure 7:
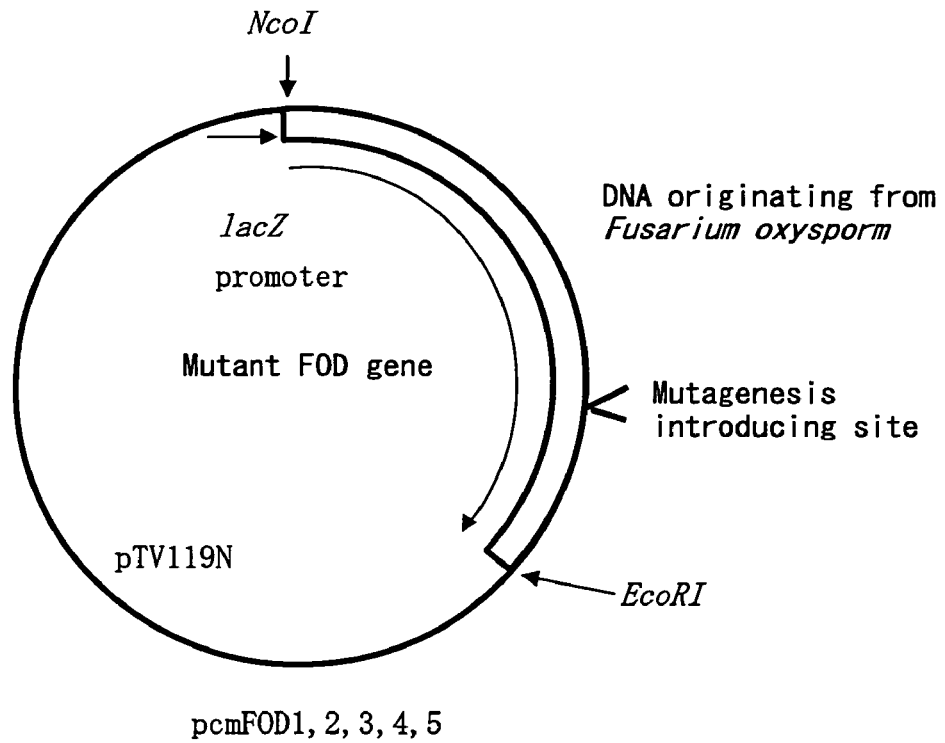
FIG. 7 shows a structure common to plasmids pcmFOD1 to pcmFOD5 of Example 20 of the present invention.

In the Table, "below limit" indicates "below the detection limit" and "N.D." indicates "no data." The above results confirmed that if the 372nd lysine in the amino acid sequence in the sequence table Sequence ID No. 1 is replaced with another amino acid, the reactivity of FOD with glycated lysine can be relatively reduced in comparison with the reactivity with glycated valine. In particular, the mutants obtained by replacing the lysine with tryptophan, methionine, or valine were found to possess high glycated valine specificity and excellent enzyme properties. The mutant obtained by replacing the lysine with tryptophan was named FOD-W, the expression plasmid producing the FOD-W was named pcmFOD3, the mutant obtained by replacing the lysine with methionine was named FOD-M, the expression plasmid producing the FOD-M was named pcmFOD4, the mutant obtained by replacing the lysine with valine was named FOD-V, and the expression plasmid producing the FOD-V was named pcmFOD5. FIG. 7 shows a common structure for the plasmids.

EXAMPLE 21

<Assaying Fructosyl-L-Valine (FV) after Eliminating ε-Fructosyl-L-lysine (ZFL) in a Sample>

Reaction Reagent 1

| 50 mM | Tris-HCl buffer solution (pH 7.5) |
|---|---|
| 10 U/ml | FOD-V |
| 5 U/ml | Catalase |

Reaction Reagent 2

| 50 mM | Tris-HCl buffer solution (pH 7.5) |
|---|---|
| 10 U/ml | FOD |
| 20 U/ml | Peroxidase |
| 0.05% | Sodium azide |
| 0.04% | 4-Aminoantipyrine |
| 0.04% | TOOS |

Sample Solutions: 0.3 Mm ZFL Solutions with FV Added to a Final Concentration of 0, 0.1, 0.2, or 0.3 mM.

After preheating 0.5 ml of the reaction solution 1 at 37° C. for 5 minutes, 0.05 ml of the above sample solutions were added and reacted at 37° C. for 5 minutes. Then, 0.5 ml of the reaction solution 2 was added, and 5 minutes thereafter the absorbance at 555 nm was measured. Distilled water was used instead of the sample solution for a blank test. As a control, a reaction solution 1 was processed in the same manner without adding FOD-V.

Figure 8:
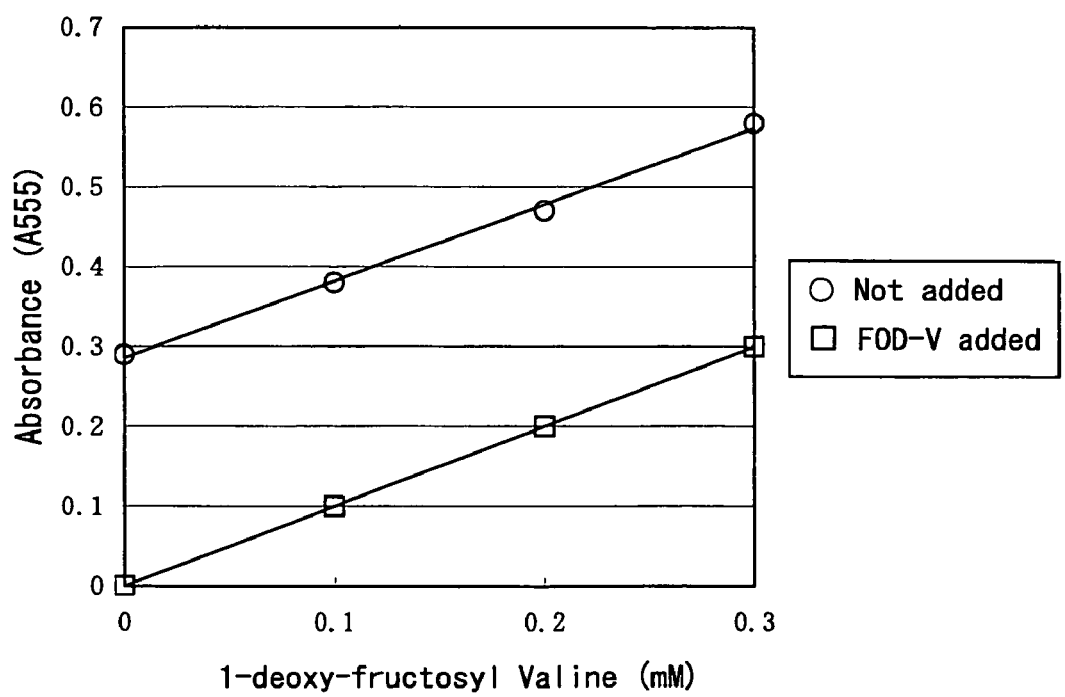
FIG. 8 is a graph showing the result of absorbance measurement at a wavelength of 555 nm of the glycated valine concentration measuring reaction solution from which glycated lysine has been removed using the mutant fructosyl amino acid oxidase in Example 21 of the present invention and the reaction solution with no removing treatment.

In FIG. 8, open circles indicate the results obtained without adding FOD-V and open squares indicate the results obtained by adding FOD-V.

As can be seen from FIG. 8, the combined use of FOD-V and FOD ensures quantitative determination of FV after eliminating ZFL in the sample solutions.

The amino acid sequences obtained by replacing the 372nd lysine in the amino acid sequence in the sequence table Sequence ID No. 1 with tryptophan, methionine, and valine are shown in the sequence table Sequence ID No. 2, 3, and 4 respectively.

EXAMPLE 22

<Determination of Glycated Albumin Ratio>

R-1 Proteolytic Reagent

| | |
|---|---|
| 50 mM | POPSO acid buffer solution (manufactured by Wako Pure Chemical Industries, Ltd.) pH 7.5 |
| 2,500 U/ml | Protease type-XXIV (manufactured by Sigma-Aldrich Co.) |
| 1% | 3-[(3-cholamidopropyl)dimethylammonio]-2-hydroxypropane sulfonic acid (manufactured by Sigma-Aldrich Co.) |
| 5 U/ml | Ascorbic acid oxidase (manufactured by F. Hoffmann-La Roche Ltd.) |
| 5% | DMSO |
| 5 m | 4-Aminoantipyrine |

R-2 Glycated Amino Acid Assay Reagent

| | |
|---|---|
| 150 mM | HEPES acid buffer solution (manufactured by Wako Pure Chemical Industries, Ltd.) pH 7.5 |
| 5 mM | TODB |
| 10 U/ml | POD |
| 20 U/ml | R-FOD-II |
| 3% | Glutamic acid |

R-3 Albumin Pretreatment Reagent

| | |
|---|---|
| 10 mM | Tris-HCl buffer solution (pH 8.0) |
| 0.3% | Sodium lauryl sulfate |

R-4 Albumin Coloring Reagent

| | |
|---|---|
| 200 mM | Succinic acid buffer solution (Wako Pure Chemical Industries, Ltd.) pH 5.5 |
| 0.15 mM | Bromocresol purple (manufactured by Wako Pure Chemical Industries, Ltd.) |
| 0.3% | Tx-100 (manufactured by Wako Pure Chemical Industries, Ltd.) |

<Sample>
1. Blood serum of healthy persons and diabetics, 35 samples for each
2. Controlled blood serum H (manufactured by BML, Inc.) was used as a calibrator.

The glycated albumin concentration of the calibrator was previously adjusted so that the results of clinical sample assay by the HPLC method and the enzymatic method may coincide. The value of CRM470 was used as an albumin value.

<Reaction Procedure>

8 μl of a sample was added to 240 μl of R-1 incubated at 37° C. The reaction was initiated at 37° C. and exactly five minutes thereafter 80 μl of R-2 was added. Absorbance change at 555 nm before the addition of R-2 and five minutes after the addition of R-2 was measured. The controlled blood serum H and distilled water were measured separately to prepare a calibration curve, based on which the glycated albumin concentration in the samples was determined.

2 μl of a sample was added to 160 μl of the R-3 albumin pretreatment reagent incubated at 37° C. The reaction was initiated at 37° C. and exactly five minutes thereafter 160 μl of the albumin coloring reagent R-4 was added. Absorbance at 600 nm was measured before the addition of the albumin coloring reagent and five minutes after the addition of the albumin coloring reagent.

A calibration curve was prepared using distilled water and a sample with a known albumin concentration instead of the sample to measure albumin concentration.

GA % of the enzymatic method was determined by the formula, $$GA\% = (GA \text{ concentration}/\text{albumin concentration}) \times 100.$$

The value according to the HPLC method was measured using Hi-AUTO GAA-2000 (manufactured by ARKRAY, Inc.). The results are shown in FIG. 9.

As can be seen from FIG. 9, the enzymatic method and HPLC method showed excellent correlation of r=0.998. All these reagents exhibited no change in performance after storing in a liquid state for two weeks at 37° C. Based on these experiments, the reagents have been clearly proven to precisely assay glycated albumin and determine the glycated albumin ratio by 1) avoiding the effect of globulin components and ascorbic acid,
2) stabilizing proteases and enzymes that react at least with a glycated amino acid,
3) precisely assaying albumin, and
4) avoiding the effect of glycated hemoglobin.

EXAMPLE 23

<Using an Enzyme Reacting at Least with a Glycated Amino Acid for the First Reagent and a Composition Containing a Protease for the Second Reagent>

R-1

| | |
|---|---|
| 200 mM | POPSO buffer solution (pH 7.5) |
| 5 mM | 4-Aminoantipyrine |
| 10 U/ml | POD |
| 20 U/ml | R-FOD |
| 5 U/ml | Ascorbic acid oxidase |
| 3% | Glutamic acid |

R-2

| | |
|---|---|
| 20 mM | Piperazine-1,4-bis(2-ethanesulfonic acid) buffer solution (pH 6.5) |
| 20% | DMSO |
| 8,000 U/ml | Protease type-XXIV |
| 4% | 3-[(3-cholamidopropyl)dimethylammonio]-2-hydroxypropane sulfonic acid |
| 5 mM | TODB |

R-3, R-4

The same as in Example 22.

<Sample>

The same sample as t in Example 22 and 10-200 μM FZL

<Reaction Procedure>

The same as in Example 22.

The results are shown in FIG. 23.

As can be seen from FIG. 23, glycated proteins were excellently assayed in a short reaction time of 10 minutes even in the case where an enzyme reacting at least with a glycated amino acid is added to the first reagent and a protease is added to the second reagent. In addition, even if a glycated amino acid is present in a sample, the glycated amino acid in the sample can be eliminated by the enzyme reacting at least with the glycated amino acid formulated in R-1, thereby enabling the glycated proteins to be precisely assayed.

The reagent of the present invention exhibited a good correlation (R=0.99) with the HPLC method of:

Enzymatic method $GA\% = 1.03 \times HPLC$ method $GA\% - 0.3$ confirming precise assay of glycated proteins. There was no decrease in performance of the reagent of the present invention after storing for three weeks at 37° C. or for 15 months in a refrigerator.

INDUSTRIAL APPLICABILITY

The ratio of glycated proteins and glycated albumin in samples can be precisely determined by the present invention. Therefore, the composition of the present invention can be effectively utilized as a clinical inspection agent.

REMARKS TO DEPOSITED BIOLOGICAL MATERIALS (1) (a) Name and address of the organization to which the biological materials have been deposited: Name: The International Patent Organism Depositary, National Institute of Advanced Industrial Science and Technology, Independent Administrative Institution Address: Central 6, 1-1-1 Higashi, Tsukuba-shi, Ibaraki, 305-8566, Japan (b) Date of deposition to the deposition organization (a) Jan. 16, 2001

(c) Number of deposition given by the deposition organization (a): FERM BP-7847

(2) (a) Name and address of the organization in which the biological materials have been deposited: Name: The International Patent Organism Depositary, National Institute of Advanced Industrial Science and Technology, Independent Administrative Institution Address: Central 6, 1-1-1 Higashi, Tsukuba-shi, Ibaraki, 305-8566, Japan (b) Date of deposition to the deposition organization of (a): Jan. 16, 2001

(c) Number of deposition given by the deposition organization (a): FERM BP-7848

The invention claimed is:

1. A composition for assaying glycated proteins comprising a proteolytic reagent and a glycated amino acid assay reagent,
   characterized in that the proteolytic reagent comprises a protease and at least one selected from the group consisting of deoxycholic acid, deoxycholic acid amide, cholic acid amide, octyl glucoside, a quaternary ammonium salt, a quaternary ammonium salt-type cationic surfactant, concanavalin A, and betaine,
   and the glycated amino acid assay reagent comprises fructosyl amino acid oxidase.

2. The composition according to claim 1, wherein the deoxycholic acid amide is bisgiuconamidopropyldeoxycholamide, and the cholic acid amide is 3-[(3-cholamidopropyl)dimethylammonio]propane sulfonic acid, 3-[(3-cholamidopropyl)dimethylammonio]-2-hydroxypropane sulfonic acid, or bisgiuconamidopropyicholamide.

3. The composition according to claims 1 or 2, characterized in that the composition is liquid, and a protease stabilizer selected from the group consisting of dimethylsulfoxide, ethanol, a quaternary ammonium salt, and a quaternary ammonium salt-type cationic surfactant is added to the proteolytic reagent comprising the protease.

4. A liquid composition for assaying glycated proteins comprising a protolytic reagent comprising a protease and a glycated amino acid assay reagent comprising a fructosyl amino acid oxidase,
   characterized in that the proteolytic reagent comprises a protease stabilizer selected from the group consisting of dimethylsulfoxide, ethanol, a quaternary ammonium salt and a quaternary ammonium salt-type cationic surfactant, and said protease retains relative sensitivity of 70% or more after being stored for one day at 37° C.

5. The composition according to claims 1 or 2, characterized in that the composition is liquid, and a stabilizer for the fructosyl amino acid oxidase selected from the group consisting of sugar alcohol, sorbitol, trehalose, sucrose, ammonium sulfate, an amino acid, and sarcosine is added to the glycated amino acid assay reagent.

6. A liquid composition for assaying glycated proteins comprising a protolytic reagent comprising a protease and a glycated amino acid assay reagent comprising a fructosyl amino acid oxidase,
   characterized in that the glycated amino acid assay reagent comprises a stabilizer for said enzyme selected from the group consisting of sugar alcohol, sorbitol, sucrose, trehalose an ammonium sulfate, amino acid, and sarcosine, and said enzyme retains relative sensitivity of 60% or more after being stored for two days at 37° C.

7. The composition according to claims 1 or 2, wherein the protease is originated from a naturally occurring or genetically engineered microorganism belonging to the genus *Bacillus*.

8. The composition according to claims 1 or 2, wherein the fructosyl amino acid oxidase is a mutant fructosyl amino acid oxidase of which the reactivity with glycated valine has been significantly decreased by replacing the $372^{nd}$ lysine in SEQ ID NO.: 1 with another amino acid.

9. The composition according to claim 8, wherein the $372^{nd}$ lysine of the mutant fructosyl amino acid oxidase is replaced with tryptophan, methionine, or valine.

10. A method for assaying glycated proteins using a protease and fructosyl amino acid oxidase, characterized in that the protease is reacted
    in the presence of at least one selected from the group consisting of deoxycholic acid, a deoxycholic acid amide, a cholic acid amide, a quaternary ammonium salt, a quaternary ammonium salt-type cationic surfactant, concanavalin A, octyl glucoside, and betaine to decrease the reactivity of the protease with globulin components.

11. The method according to claim 10, wherein the deoxycholic acid amide is bisgluconamidopropyldeoxycholamide, and the cholic acid amide is 3-[(3-cholamidopropyl)dimethylammonio]propane sulfonic acid, 3-[(3-cholamidopropyl)dimethylammonio]-2-hydroxypropane sulfonic acid, or bisgiuconamidopropyicholamide.

12. The method according to claims 10 or 11, wherein a protease stabilizer selected from the group consisting of dimethylsulfoxide, ethanol, a quaternary ammonium salt, and a quaternary ammonium salt-type cationic surfactant is added to the protease.

13. A method for assaying glycated proteins using a protease and a fructosyl amino acid oxidase, characterized in that a protease stabilizer selected from the group consisting of dimethylsulfoxide, ethanol, a quaternary ammonium salt, and a quaternary ammonium salt-type cationic surfactant is added to the protease, and the protease retains relative sensitivity of 70% or more after being stored for one day at 37° C.

14. The method according to claims 10, 11, or 13, wherein a stabilizer selected from the group consisting of sugar alcohol, sorbitol, sucrose, trehalose, ammonium sulfate, an amino acid, and sarcosine is added to the fructosyl amino acid oxidase.

15. A method for assaying glycated proteins using a protease and a fructosyl amino acid oxidase characterized in that a stabilizer for the oxidase selected from the group consisting of sugar alcohol, sorbitol, sucrose, trehalose, ammonium sulfate, an amino acid, and sarcosine is added to the oxidase, and the oxidase retains relative sensitivity of 60% or more after being stored for two days at 37° C.

16. The method according to claims 10, 11, 13, or 15, wherein the protease is originated from a naturally occurring or genetically engineered microorganism belonging to the genus *Bacillus*.

17. The method according to claims 10, 11, 13, or and 15, wherein the composition is a liquid product.

18. The method according to claim 17, wherein the glycated proteins are assayed by reacting the sample with the fructosyl amino acid oxidase and then with the protease.

19. The method according to claim 10, wherein the enzyme is a mutant fructosyl amino acid oxidase of which the reactivity with glycated valine has been significantly decreased by replacing the 372nd lysine in the amino acid sequence in SEQ ID NO.: 1 with another amino acid.

20. The method according to claim 19, wherein the 372nd lysine of the mutant fructosyl amino acid oxidase is replaced with tryptophan, methionine, or valine.

* * * * *